(12) United States Patent
Tsay et al.

(10) Patent No.: US 11,484,714 B2
(45) Date of Patent: *Nov. 1, 2022

(54) COCHLEAR IMPLANT LOCALIZATION SYSTEM

(71) Applicant: Medtronic Xomed, Inc., Jacksonville, FL (US)

(72) Inventors: Ishan Ann Tsay, Louisville, CO (US); Brad Jacobsen, Erie, CO (US); Nicholas J. Rawluk, Jacksonville, FL (US); Shai Ronen, Louisville, CO (US)

(73) Assignee: Medtronic Xomed, Inc., Jacksonville, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/020,141

(22) Filed: Sep. 14, 2020

(65) Prior Publication Data
US 2020/0406038 A1 Dec. 31, 2020

Related U.S. Application Data

(63) Continuation of application No. 15/890,920, filed on Feb. 7, 2018, now Pat. No. 10,773,082.

(51) Int. Cl.
*A61N 1/36* (2006.01)
*A61B 34/20* (2016.01)
(Continued)

(52) U.S. Cl.
CPC .......... *A61N 1/36039* (2017.08); *A61B 34/20* (2016.02); *A61B 90/37* (2016.02);
(Continued)

(58) Field of Classification Search
CPC ............ A61N 1/36039; A61N 1/0541; A61N 1/36038; A61B 34/20; A61B 90/37;
(Continued)

(56) References Cited

U.S. PATENT DOCUMENTS 4,352,960 A 10/1982 Dormer et al.
5,697,377 A 12/1997 Wittkampf
(Continued)

OTHER PUBLICATIONS

Cochlear™ Nucleus® CI512 cochlear implant Technical Specifications, 2 pages, 2009.
(Continued)

*Primary Examiner* — Catherine M Voorhees
(74) *Attorney, Agent, or Firm* — Harness, Dickey & Pierce, P.L.C.

(57) ABSTRACT

A navigation system or combination of navigation systems can be used to provide one or more navigation modalities to track a position and navigate a single instrument in a volume. For example, both an Electromagnetic (EM) and Electropotential (EP) navigation system can be used to navigate an instrument within the volume. The two navigation systems may be used separately to selectively individually navigate the single instrument in the volume. Disclosed are also systems and processes to determine a shape of the single instrument either alone or in combination with the position of the instrument. The instrument may be navigated with the addition of tracking devices or with native or inherent portions of the instrument.

19 Claims, 8 Drawing Sheets

(51) Int. Cl.
  *A61N 1/05* (2006.01)
  *A61B 90/00* (2016.01)
  *A61B 5/06* (2006.01)

(52) U.S. Cl.
  CPC ............ *A61N 1/0541* (2013.01); *A61B 5/068* (2013.01); *A61B 2034/2051* (2016.02); *A61B 2034/2053* (2016.02); *A61B 2034/2072* (2016.02); *A61B 2090/374* (2016.02); *A61B 2090/3762* (2016.02); *A61N 1/36038* (2017.08)

(58) Field of Classification Search
  CPC ............ A61B 5/068; A61B 2034/2051; A61B 2034/2053; A61B 2034/2072; A61B 2090/374; A61B 2090/3762
  See application file for complete search history.

(56) References Cited

U.S. PATENT DOCUMENTS

| | | | |
|---|---|---|---|
| 5,983,126 A * | 11/1999 | Wittkampf | A61B 5/283 |
| | | | 600/509 |
| 6,038,484 A | 3/2000 | Kuzma | |
| 7,462,175 B2 | 12/2008 | Chang et al. | |
| 7,599,730 B2 | 10/2009 | Hunter et al. | |
| 7,697,972 B2 | 4/2010 | Verard et al. | |
| 7,971,341 B2 | 7/2011 | Dukesherer et al. | |
| 8,010,210 B2 | 8/2011 | Rau et al. | |
| 8,086,319 B2 | 12/2011 | van Dijk | |
| 8,260,395 B2 | 9/2012 | Markowitz et al. | |
| 8,260,437 B2 | 9/2012 | Llinas et al. | |
| 8,473,075 B2 | 6/2013 | Gallegos et al. | |
| 8,494,613 B2 | 7/2013 | Markowitz et al. | |
| 8,494,614 B2 | 7/2013 | Markowitz et al. | |
| 8,644,907 B2 | 2/2014 | Hartmann et al. | |
| 8,712,554 B2 | 4/2014 | Beerling et al. | |
| 9,101,285 B2 | 8/2015 | Markowitz et al. | |
| 9,211,403 B2 | 12/2015 | Tortonese et al. | |
| 9,345,397 B2 | 5/2016 | Taylor et al. | |
| 10,751,132 B2 | 8/2020 | Tsay et al. | |
| 10,773,082 B2 * | 9/2020 | Tsay | A61N 1/0541 |
| 2006/0052656 A1 | 3/2006 | Maghribi et al. | |
| 2010/0030312 A1 | 2/2010 | Shen | |
| 2010/0292759 A1 * | 11/2010 | Hahn | A61N 1/37518 |
| | | | 607/57 |
| 2013/0066228 A1 | 3/2013 | Capcelea et al. | |
| 2014/0228669 A1 * | 8/2014 | Carter | A61N 1/0541 |
| | | | 600/409 |
| 2014/0350640 A1 | 11/2014 | Patrick et al. | |
| 2015/0314122 A1 | 11/2015 | Kabot et al. | |
| 2015/0320550 A1 * | 11/2015 | Downing | A61N 1/0541 |
| | | | 607/137 |
| 2016/0001077 A1 | 1/2016 | Pontoppidan et al. | |
| 2016/0059015 A1 * | 3/2016 | Risi | A61N 1/36038 |
| | | | 607/57 |
| 2019/0025040 A1 | 1/2019 | Andreason et al. | |
| 2019/0239959 A1 | 8/2019 | Tsay et al. | |
| 2019/0240488 A1 | 8/2019 | Tsay et al. | |
| 2019/0261099 A1 | 8/2019 | Crawford et al. | |

OTHER PUBLICATIONS

Cochlear™ Nucleus® implant portfolio, www.cochlear.com/wps/wcm/connect/intl/home/discover/cochlear-implants/nucleus-implant-portfolio, 2 pages, 2017.

Cochlear™ Nucleus® Kanso® Sound Processor, www.cochlear.com/wps/wcm/connect/intl/home/discover/cochlear-implants/kanso-sound-processor, 2 pages, 2017.

Cochlear™ Nucleus® System, https://www.cochlear.com/us/for-professionals/products/c . . . , 5 pages, 2017.

Cochlear™ Surgical Techniques for the Contour Advance, www.cochlear.com/wps/wcm/connect/us/for-professionals/products/c . . . , 2 pages, 2017.

* cited by examiner

COCHLEAR IMPLANT LOCALIZATION SYSTEM

CROSS-REFERENCE TO RELATED APPLICATIONS

This application is a continuation of U.S. patent application Ser. No. 15/890,920 filed on Feb. 7, 2018.

This application also includes subject matter related to subject matter disclosed in U.S. patent application Ser. No. 15/890,882, entitled COCHLEAR IMPLANT LOCALIZATION SYSTEM and U.S. patent application Ser. No. 15/890,949, entitled COCHLEAR IMPLANT LOCALIZATION SYSTEM, each filed on Feb. 7, 2018. The entire disclosures of each of the above applications are incorporated herein by reference.

FIELD

The present disclosure relates generally to a system for localizing a tracked item, and particularly to a localization system using one or more modalities for localizing the item within a volume.

BACKGROUND

This section provides background information related to the present disclosure which is not necessarily prior art.

A navigation system can be used to track and navigate an instrument within a volume. For example, a navigation system can be used to track an electromagnetic tracking device on an instrument during a surgical procedure. The tracking device is localized to determine its location.

Certain instruments, however, are not associated with a tracking device. Thus, certain instruments are not trackable with a navigation system. Instruments that are not trackable may require direct inspection to be certain of final location. Moreover, it may be difficult to associate tracking hardware with such instruments due to various constraints.

SUMMARY

This section provides a general summary of the disclosure, and is not a comprehensive disclosure of its full scope or all of its features.

A navigation system or combination of navigation systems can be used to provide navigation for tracking an instrument. The instrument may be an instrument to assist in a procedure and/or may be a permanently implanted device. Permanently implantable devices may include generally known devices such as cochlear implants, including the Contour Advance® and/or Nucleus® cochlear implants sold by Cochlear Americas having a place of business at Centennial, Colo. USA Cochlear implants may include a plurality of electrodes spaced apart along a length of an implantable device. The implantable device may, therefore, be an implant. The implant may be connected to an external device for various purposes, such as receiving, amplifying, and/or providing stimulation. Operation of cochlear implants is well known to one skilled in the art to receive audio signals and provide stimulation within a cochlea to replicate hearing.

Navigation systems may include one or more types of navigation or modalities of navigation to navigate a single instrument. The single instrument can be positioned within the patient and tracked. For example, both an Electromagnetic (EM) and Electropotential (EP) tracking systems can be used to navigate an instrument within a patient. Various EM navigation systems including those disclosed in U.S. Pat. Nos. 7,599,730 and 7,697,972, both incorporated herein by reference. Various EP navigation systems include those disclosed in U.S. Pat. Nos. 8,260,395 and 9,101,285, both incorporated herein by reference. Certain navigation systems may incorporate and/or operate with two types of navigation modalities, such as both EM and EP, and include those disclosed in U.S. Pat. Nos. 8,494,613 and 8,494,614, incorporated herein by reference.

A navigation system can generally include a localizer and a tracking device. One skilled in the art will understand that the localizer can either transmit or receive a signal and the tracking device can also transmit or receive a signal to allow for a determination of a location of the tracking device associated with the surgical instrument. A surgical instrument can have associated therewith one or more tracking devices for navigation, as discussed herein. Also, each tracking device may be used in one or more modalities of navigation. For example, an instrument may include an electrode that can be used with an EP tracking system and can also be associated or moved relative to a tracking device that includes an EM coil to be used with an EM tracking system.

An instrument may include one or more tracking devices to be used with one or more navigation systems during a single procedure. In addition, a method can be used to register the two navigation systems during a single procedure. The registration of the two navigation systems can allow all or a determination of a selected number of points within one navigational domain to coordinate or correspond to all or a selected number of points in a second navigational domain.

The instrument may also include one or more tracking devices that may be used with a single selected navigation system of a single selected modality. In various embodiments, portions of an instrument (including an implant) may be used as tracking devices during an implantation procedure. The same portions may, after implantation, be repurposed as or re-tasked as augmenting portions.

It is understood, that although the following disclosure specifically relates to a cochlear implant that other types of implants may be used. A cochlear implant, as discussed herein, includes various portions that may be useful during an implantation procedure for navigation purposes, but may be repurposed after implantation for stimulation of a patient. In other words, the cochlear implant may have portions (e.g. electrodes) that operate for a first function and are then changed to a different function. The cochlear implant may include a plurality of electrodes that are connected to a receiver and stimulator (R&S) for use. The R&S may receive a signal and provide a stimulation signal to the electrodes, during use after implantation. Prior to implantation, the electrodes may be used for tracking so that the hardware of the implant need not be altered or augmented. Standard construction of the cochlear implant, therefore, may be maintained. As discussed herein, various additional tracking devices may be added, however, to the cochlear implant.

Further, it is understood, that the systems and methods disclosed herein are not limited to use during implantation into a human, but may also be useful during navigation of an instrument relative to any non-living machine having selected or appropriate characteristics.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 1:
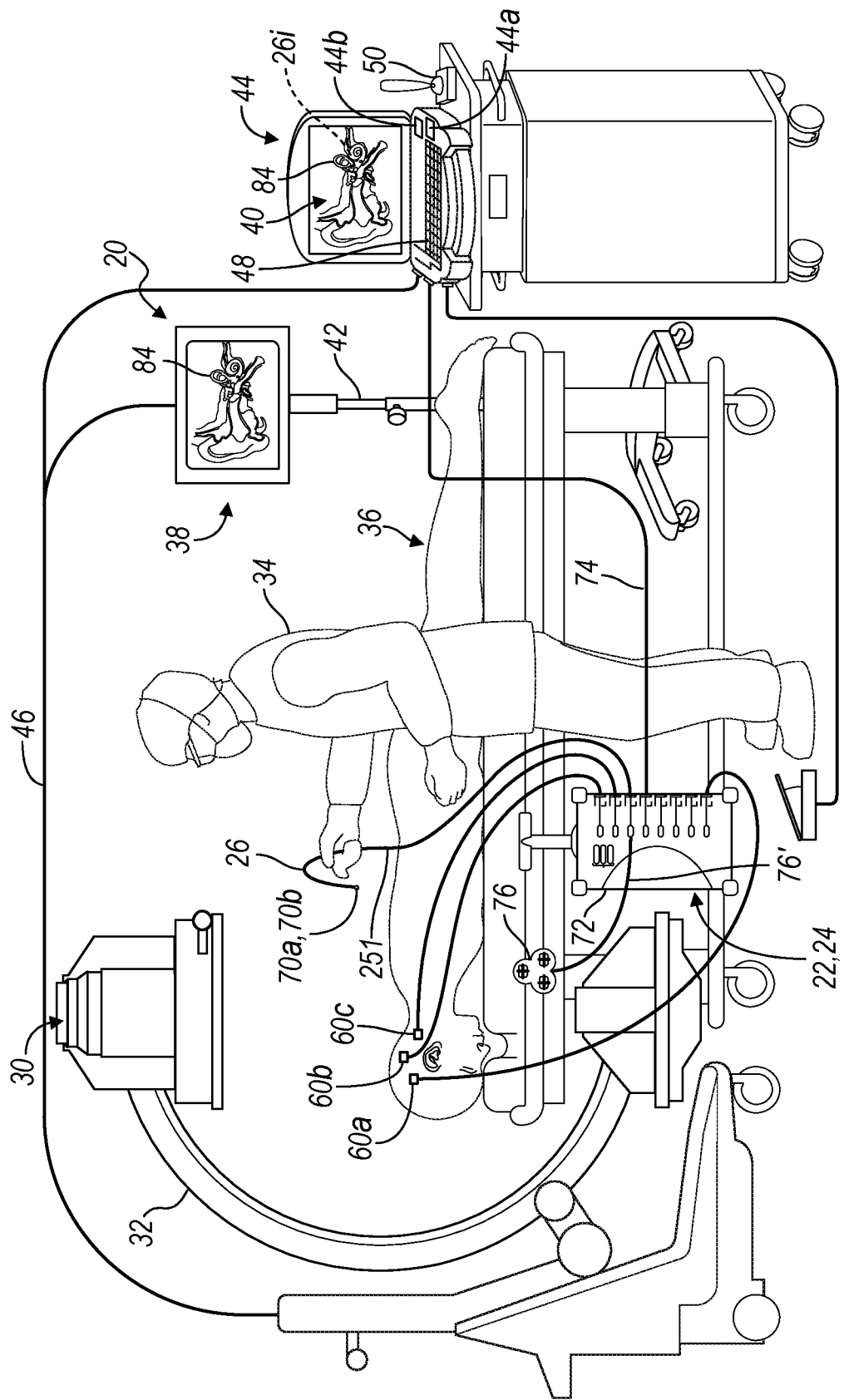
FIG. 1 is an environmental view of a navigation system.
Figure 7:
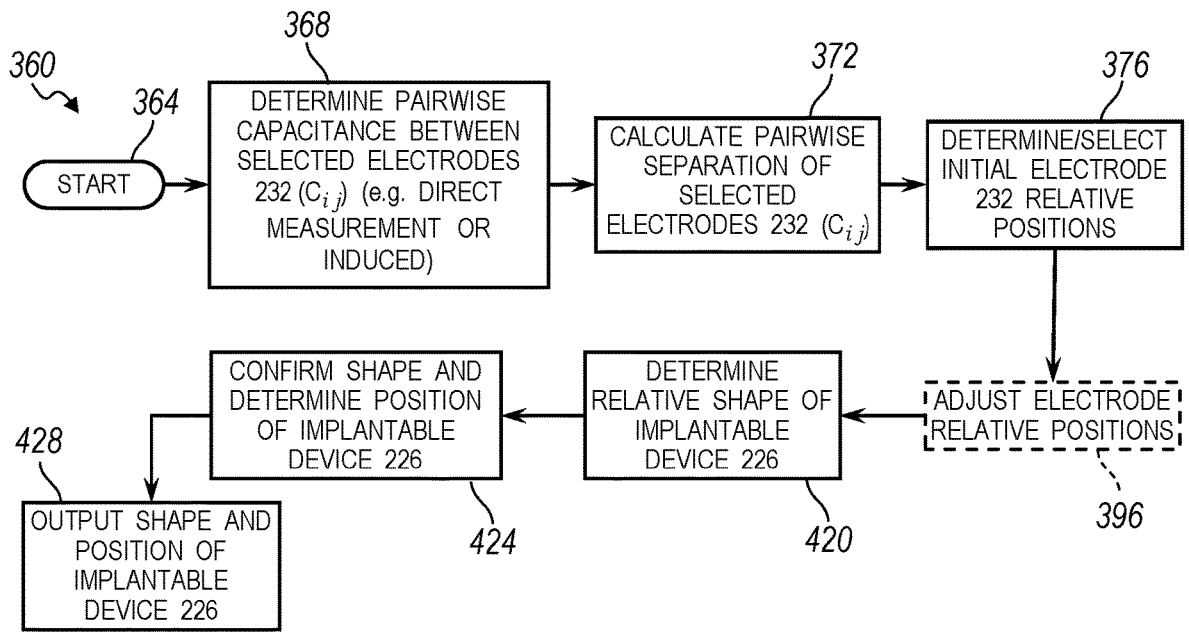
Figure 7A:
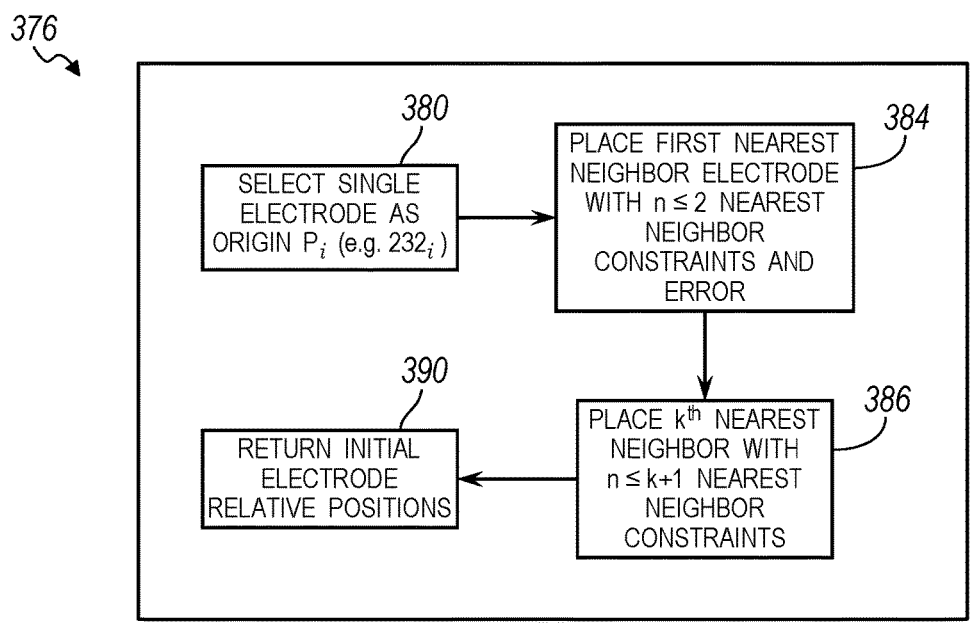
Figure 7B:
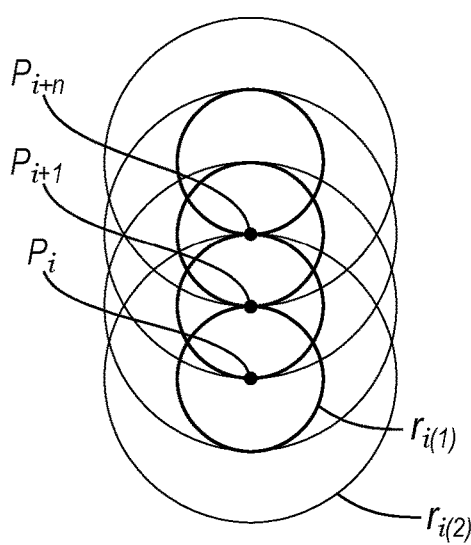
Figure 7B:
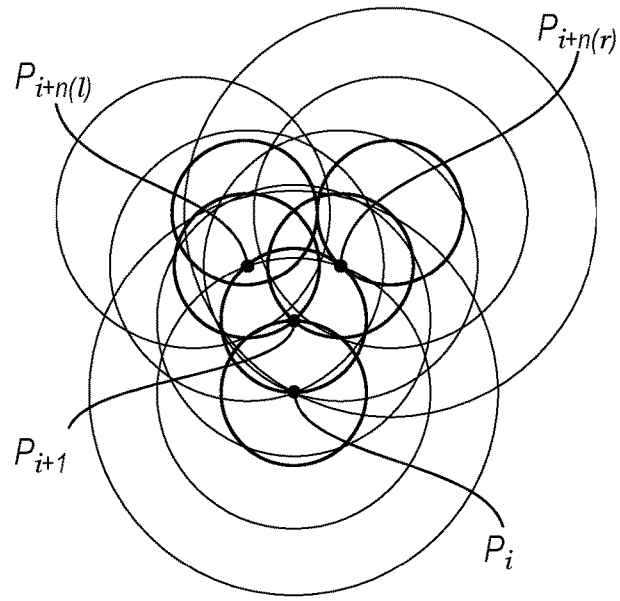
Figure 7B:
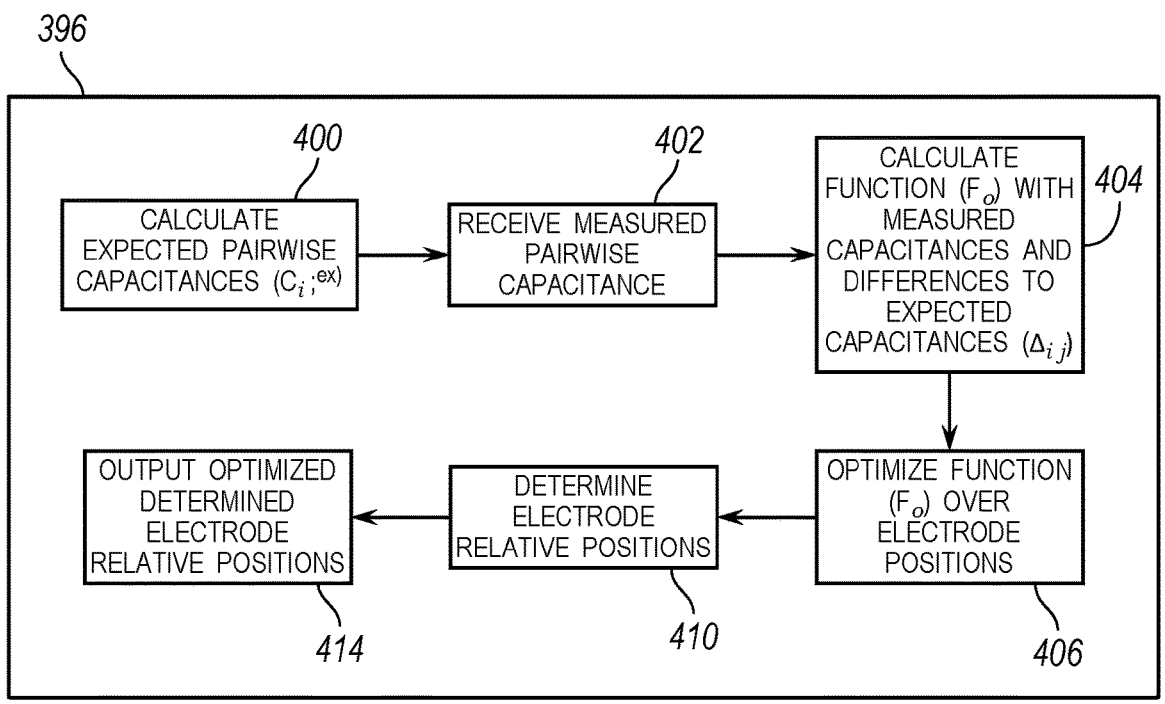
Figure 8:
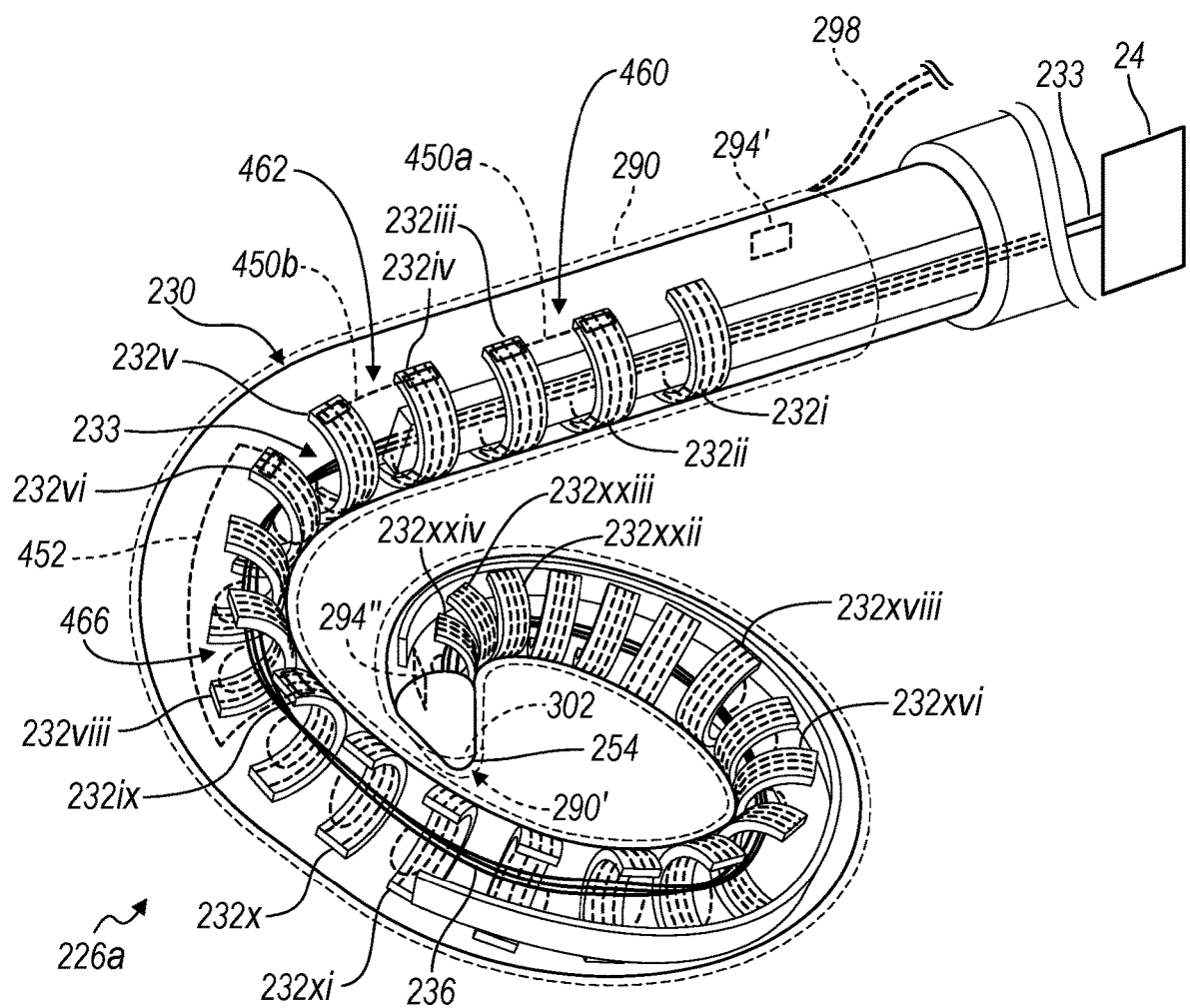

FIGS. 7, 7A, and 7B is a flowchart illustrating a method of determining a shape of an implantable device, and sub-routines thereof;

FIGS. 7A1 and 7A2 illustrate theoretical shapes based on capacitances between multiple electrodes; and FIG. 8 is a perspective view of an implantable device, according to various embodiments.

Corresponding reference numerals indicate corresponding parts throughout the several views of the drawings.

DETAILED DESCRIPTION

Example embodiments will now be described more fully with reference to the accompanying drawings.

Figure 2A:
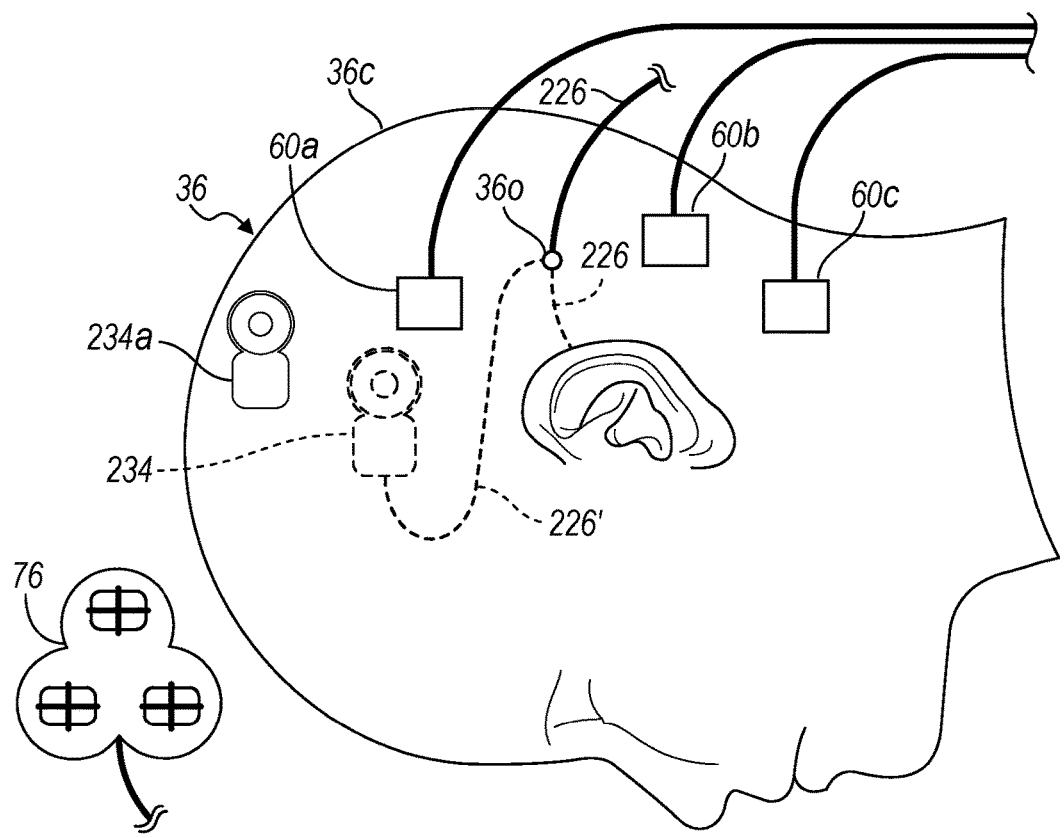
FIG. 2A is a detailed view of a subject and localizer portions, according to various embodiments.

A navigation system 20 is illustrated in FIG. 1, and in further detail in FIG. 2A, that may be a surgical navigation system. A first tracking system can include an electropotential (EP) tracking system 22. A second tracking system can include an electromagnetic (EM) tracking system 24. Appropriate EP tracking systems may include those disclosed in U.S. Pat. Nos. 8,260,395 and 9,101,285, both incorporated herein by reference. Appropriate EM navigation systems include those disclosed in U.S. Pat. Nos. 7,599,730 and 7,697,972, both incorporated herein by reference. The first and second tracking systems 22, 24 can be used to track one or more instruments, such as a single surgical instrument 26. The surgical instrument 26 can be any appropriate instrument, including a cochlear implant that is positioned in a cochlea of an inner ear of a subject. Other appropriate instruments may also include but not limited to, cardiac, brain, spinal, sacral, vagal, and gastric electrode implants such as a lead used as a part of an implantable medical device (IMD) for heart rhythm treatment, neurological treatment, ablation, or other appropriate purposes.

The navigation system 20 may be operated with only a single one of the tracking systems 22, 24, each provided in a selected separate modality. The first tracking system 22 being an EP modality tracking system and the second tracking system 24 being an EM modality tracking system. The navigation system 20, therefore, may be a single or multiple modalities tracking system.

In certain procedures, having two tracking systems can be useful. Exemplary procedures include placing a cochlear implant with one or more electrodes in a cochlea of a subject, such as a human subject or patient 36. In the cochlea, an electrode on an implant may be exposed to a conductive fluid for position determination with the EP tracking system 22. Also, a tracking device that may transmit or receive an EM signal may be tracked with the EM tracking system 24. Also, registration of the EM tracking system 24 to image data can be used to assist in illustrating a position, such as an anatomical position or anatomy, relative to the patient 36.

Certain procedures also may be more easily tracked with the EP tracking system 22 as opposed to the EM tracking system 24. For example, a stylet including an EM tracking device can be positioned through at least a portion the implant or delivery portion of the implant. In various procedures, however, the stylet can be removed from a portion of the implant to allow the implant to be substantially less rigid and more flexible. Once the stylet is removed from the implant the exact position of the implant may not be trackable with the EM tracking system 24. When the stylet is removed, the implant electrode can be tracked with the EP tracking system 22.

The navigation system 20 used in the various procedures discussed above or herein, can also include various components in addition to the tracking systems 22, 24, such as an imaging system 30. The imaging system 30 can be any appropriate imaging system and is exemplary illustrated as a fluoroscopic C-arm system 32. Other imaging systems can include computed tomography (CT) imaging systems, O-Arm® imaging system, magnetic resonance imaging (MRI) systems, and positron emission tomography (PET) imaging systems. The imaging system 30 can be used by a surgeon 34 to image the patient 36 prior to (preoperatively), during (intraoperatively), or after (postoperatively) a procedure. Imaging the patient 36 can create image data that can be viewed as an image 84 on a display device 38 or a display device 40. The display device 38, 40 can be provided alone, such as on a stand 42 or with a processing system as a part of a workstation or processing system 44. The image data can be transferred from the imaging system 30 through a data transmission system 46, such as a wired or wireless transmission system, to the display devices 38, 40. Images may be selected and appropriate for a selected procedure, such as that of an inner ear or cochlea for a cochlear implant.

The navigation system 20, also including the tracking systems 22, 24 can be incorporated or connected to the processor system 44. The processor system 44 can include human input devices such as a keyboard 48, a joystick or mouse 50, a foot pedal 52 or any other appropriate human input device. Each of the human input devices 48-52 can be connected with the processor system 44 or other systems, such as the imaging system 30, for control or actuation thereof. The processor system may further include a general purpose processor 44a that is configured to execute instructions that are stored on a memory 44b, such as an intransatory memory (e.g. solid state memory, spinning hard-disc, optical readable disc). The processor 44a may also be a special purpose processor, such as an ASIC.

The EP tracking system 22 can include components to generate a current in the patient 36. The EP tracking system can include or be based on the Localisa™ intracardiac tracking system sold by Medtronic, Inc. having a place of business in Minneapolis, Minn. The EP tracking system 22 can also include portions disclosed in U.S. Pat. No. 5,697,377 or 5,983,126 to Wittkampf, incorporated herein by reference Briefly, the EP tracking system 22 can include one or more axis electrodes 60 (including 60a, 60b, 60c). In various embodiments the axis electrodes may be operated as pairs of axis electrodes. The axis electrodes 60 can also be referred to as a localizer, operable to generate or inject a current within a volume, such as the patient 36. The axis electrodes 60, however, may include a single axis electrode 60a. It is understood, however, that two or more axis electrodes 60b and 60c, may also be provided. With two or more electrodes, temporal variations of injected current may be used to more finely resolve the location of the implantable device, as discussed further herein.

It is also understood, that one or more pairs of axis electrodes may be provided. For example, three pairs of axis electrodes may be used to generate three substantially orthogonal axes of current within the patient 36. The axis can be defined between selected axis electrode pairs, as discussed above, by an alternating current that is generated between any pair of the axis electrodes. For example, a first pair of axis electrodes can be positioned on a left and right side of the patient 36 to define an X-axis when a current is generated between the two axis electrodes.

The injected current from the one or more axis electrodes can be used to determine or calculate a location of a tracking device 70. The tracking device 70 can include a first or EP tracking device 70a and a second or EM tracking device 70b. The EP tracking system 22 can be used to track the EP tracking device 70a. The first tracking device 70a can sense voltages or related impedances in the patient 36 based upon the induced current from the axis electrodes 60a or between pairs of axis electrodes. The voltages can be related to a position of the first tracking device 70a in the patient 36.

The axis electrodes 60a-60c can be driven with a generator in a controller 72 that is connected via wires or wirelessly with the axis electrodes 60a-64b. The generator can provide the power to generate a selected current, such as an alternating current in the patient 36. The controller 72 can also include a connection for the instrument 26 to communicate a signal from the tracking device 70 to the controller 72. The connection with the instrument 26 can be wired or wireless, according to various embodiments. In addition, the controller 72 can include a processor portion or simply be a transmitter to transmit signals from the tracking device 70. Signals can be transmitted from the controller 72 to the processor system 44 with a transmission system 74. The transmission system 74 can be a wired or wireless transmission system.

The EM tracking system 24 can also be associated with the controller 72 or can be provided with a separate controller system. It will be understood that various separate circuitry portions may be provided in the controller 72 to generate or operate the EP tracking system 22 or the EM tracking system 24.

The EM tracking system 24 includes an EM localizer 76 that can be positioned relative to the patient 36. The EM tracking system can include the AxiEM™ electromagnetic tracking system sold by Medtronic Navigation, Inc. having a place of business in Colorado, USA. The localizer 76 can generate an electromagnetic field that is sensed by the EM tracking device 70b. Alternatively, the EM tracking device 70b can generate a field that is sensed by the localizer 76.

A localizer can be used as a part of a tracking system to determine the location of the tracking device 70. For example, the localizer 76 can be interconnected with the controller 72 to transmit a signal to the processor system 44 regarding the position of the EM tracking device 70b. The axis electrodes 60a-60c can be a localizer that induces axes of current in the patient 36 to localize the EP tracking device 70a. Accordingly, the localizer can refer to a portion of the tracking system which can be exterior or interior to the volume, such as the patient 36, that is used to determine a position of the tracking device 70.

According to various embodiments, the localizer devices, including the EM localizer 76 and the axis electrodes 60a-60c, can be used to define a navigation domain in a subject space. Subject space may refer to the physical space in which the instrument is moving during a selected procedure. The subject space may include a patient space of the patient 36. Patient space can be the physical space that is being operated on during the operative procedure. The patient space can also include the navigated space through which the surgical instrument 26 is being navigated. Image space can be defined by image data that is displayed as an image 84 on the display devices 38, 40. Image data can include any appropriate image data, such as image data of a cranium, inner ear, or other appropriate portion of the patient 36. The image data is used to generate or render the image 84 that is displayed on the display devices 38, 40 and may also include atlas data. Atlas data can include statistical or historical data. The atlas data can be registered or morphed to the patient image data or patient space. It will be understood that atlas data may be used in an imageless navigation system. For example, an imageless navigation system may not require the acquisition of image data of the patient 36. The image data and atlas data may be stored or recalled from the memory 44b.

The patient space can be registered to the image space of the image data to allow a position of the instrument to be displayed (e.g. superimposed as an icon on the image 84) according to any appropriate technique, including those discussed herein. Generally, however, the patient space is registered to the image data to allow for displaying or superimposing an icon or representation of a tracked device, for example the surgical instrument 26, over the image 84 on the display device 38, 40. Registration generally allows for a transformation of the image data to the patient space. Various registration techniques can include contour matching, fiducial or point matching, automatic registration, or any other appropriate registration. For example, various landmarks or fiducials can be identified in the image data and/or image 84 and the same fiducials or landmarks can be identified in the patient 36, such as within the inner ear. The image data can then be transformed to the patient space of the patient 36 so that a proper position of a superimposed icon 26i can be shown relative to the image 84. Registration techniques can include those discussed in the U.S. Patents incorporated above.

In addition, as discussed herein, the EP tracking system 22 can be registered to the EM tracking system 24. The registration of the EP tracking system 22 to the EM tracking system 24 can allow navigation of the EP tracking device 70a with the image data 80. For example, the EP tracking system 22 may not form a localization geometry that is Euclidean to be efficiently mapped to Euclidean coordinates of an image of the subject 36. Thus, mapping or co-relating points between the EM tracking system 24 and the EP tracking system 22 allows for a point determined in the EP tracking system 22 to be translated to the EM tracking system 24 and, therefore, to the image 84. In various embodiments, co-registration may include co-locating an EM tracking device trackable with the EM tracking system 24 with an EP tracking device that is trackable by the EP tracking system 22. The co-location (e.g. placing the EM tracking device and the EP tracking device at the same position) may allow for tracking one point in space with both the EP tracking system 22 and the EM tracking system 24 to allow for registration (i.e. translation) of the two navigation spaces.

Figure 2B:
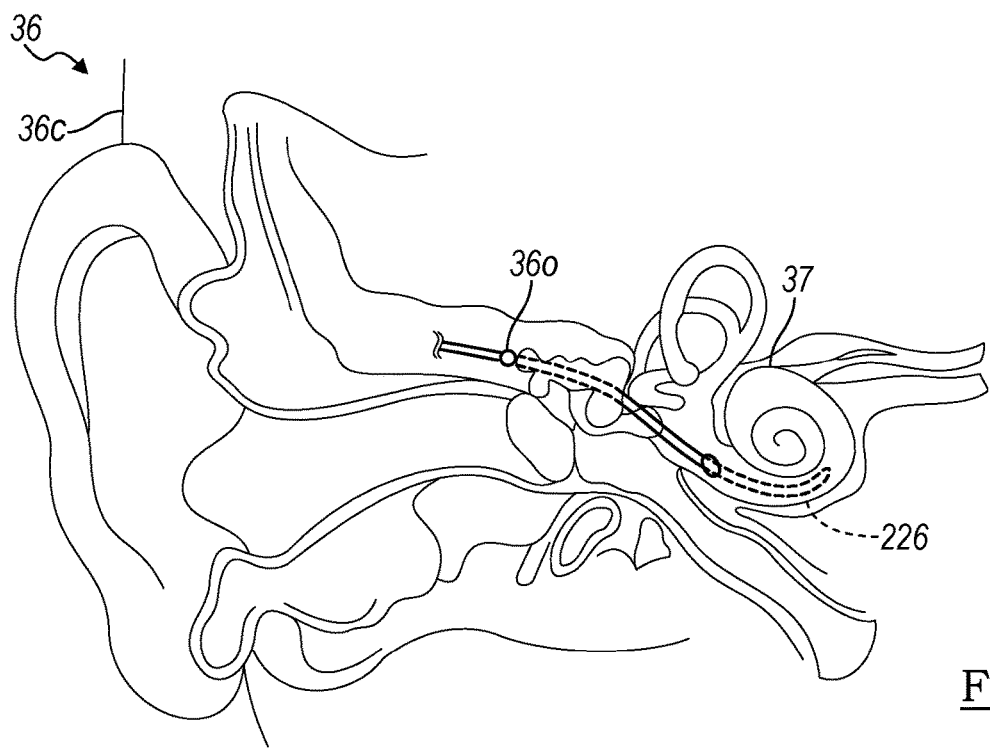
FIG. 2B is a detailed cross-section view of the subject, according to various embodiments.
Figure 3:
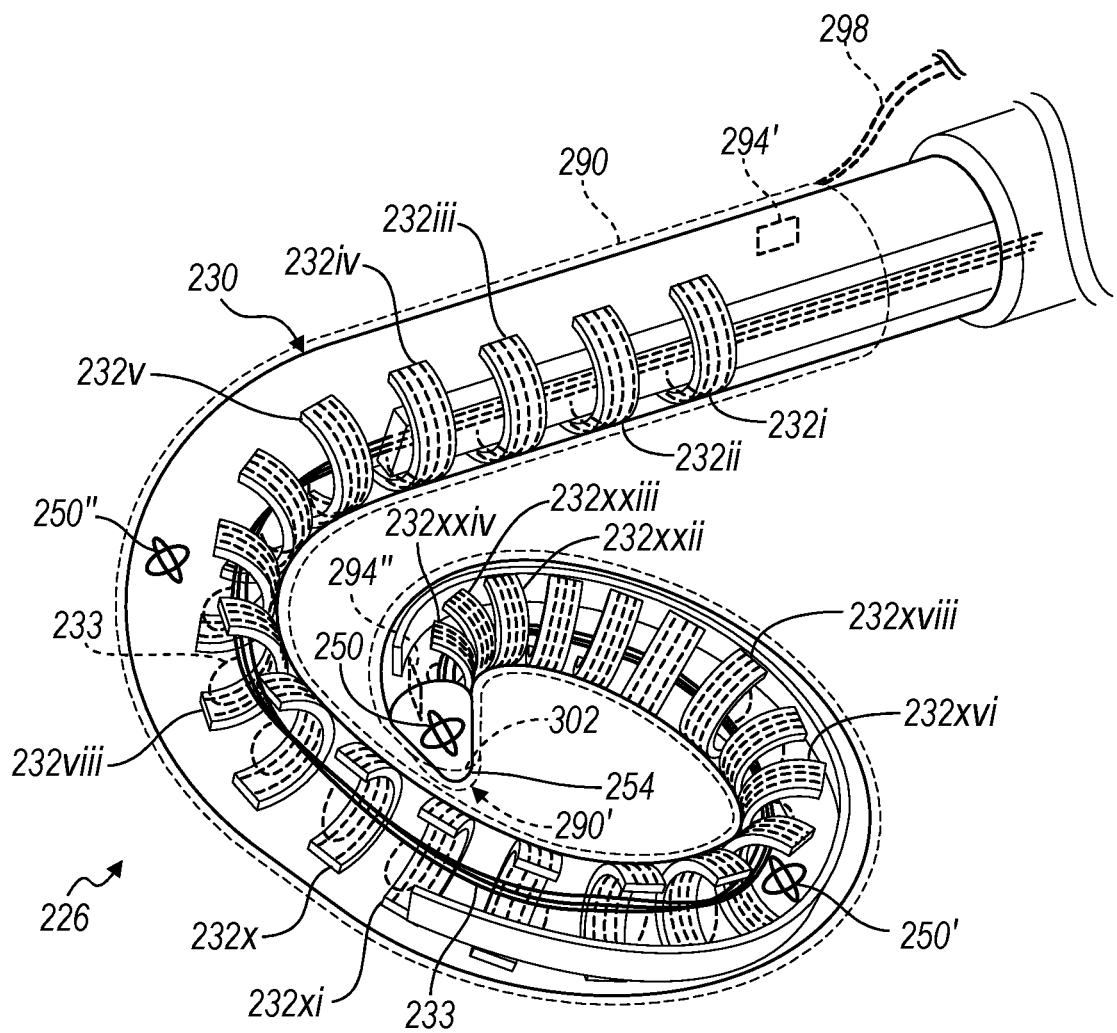
FIG. 3 is a detailed view of an instrument, according to various embodiments.

The instrument 26 may include an implantable cochlear member or cochlear implant electrode assembly 226 to be positioned within the patient 36. In various embodiments, the cochlear implant 226, as illustrated in FIG. 2B and FIG. 3, may include an elongated body 230 that extends along a long axis. The elongated body 230 may include a plurality of implant electrode or contacts, such as twenty-four individual electrode portions or contacts (also referred to individually as electrodes) 232i to 232xxiv, which is configured to be positioned within a cochlea 37 of the subject. It is understood that the cochlear implant 226 may include any appropriate number of electrodes 232 and that twenty-four electrodes is merely exemplary. Also, the cochlear implant 226 may also be referred to as an array or assembly of electrode contacts that may contact a cochlea to transmit or deliver a stimulation signal from a stimulator or source, as discussed herein.

One or more of the electrodes 232 may be formed as solid pads or members (e.g. biocompatible conductive pads (e.g. stainless steel, gold, etc.) that have a thickness that extends from the long axis of the body 230. The electrodes may also or alternatively be formed as coils of conductive material (e.g. copper, gold, carbon, etc.). The coils may be formed around a core (such as an air core) and the core may extend along an axis that is generally at an angle to and/or perpendicular to the long axis of the body 320 In various embodiments, at least a selected number, which may include all, of the electrodes may be formed as solid pads while others are formed as coils or lengths of wire. If formed as a coil of conductive material, the coils may be formed to have a geometry similar to the pads, as illustrated in FIG. 3, thus formed on a side or arc of the implantable member 226. Thus, when a coil is provided as the electrode 232, an outer most coil portion may contact the subject.

Each of the electrodes 232 may be connected with selected portions with one or more connectors, communication or transmission lines, or cables 233. Each of the electrodes 232 may have a separate line or connection 233 that allows each of the electrodes 232 to be directly connected (e.g. wired) to an internal receiver and stimulator (R&S) 234, as illustrated in FIG. 2A, and/or to an external R&S 234a, as discussed herein. Thus, the implant 226 may deliver a stimulation from the R&S 234, 234a to a selected portion of the subject 36 and/or transmit or receive other selected signals as discussed herein.

The R&S 234, 234a may be connected to the cochlear implant 226 at a selected time to provide stimulation within the cochlea 37, as is generally understood in the art. Thus, the cochlear implant may be connected to the R&S 234 as shown in phantom 226'. The R&S 234, 234a may include any appropriate R&S such as the receiver and stimulator portions and features included with the Cochlear-™Nucleus® Profile with slim Modiolar Electrode (CI532) implantable electrode system and/or Cochlear™Nucleus® Kanso® sound processor both sold by Cochlear Ltd. having a place of business at Centennial, Colo. The receiver may receive an external stimulus and provide an electrical stimulus through the one or more electrical connectors 233 to selected one or more of the electrodes 232. The connectors 233 may be conductive, and may include conductive wires or other conductive materials.

The R&S 234 may include an internal R&S 234, as illustrated in FIG. 2A, and/or an external R&S 234a. The external R&S 234a may be substantially identical to the internal R&S 234 or include selected additional or alternative components. In various embodiments, the external R&S 234a may include portions that allow for transdermal communication to an internal receiver, such as the internal R&S 234. The internal portion may then transmit the signal along the communication line 226' in a manner as discussed above, such as to the implantable electrode 226 via the connectors 233. Accordingly, the R&S 234 may include an internal portion 234 and an external R&S portion 234a. It is understood that the external portion 234a may include most or all of a power supply, a processor portion, and an audible or signal receiving portion and a transmitter to transmit to an internal R&S 234. The external component may include those portions, such as those described and further as described in U.S. Pat. No. 4,352,960, incorporated herein by reference. Further the external component may include various additional transmission features such as transmitting a signal to the CAC 22, 24 such as to assist in navigation and placement of the implant portion 226.

Figure 4:
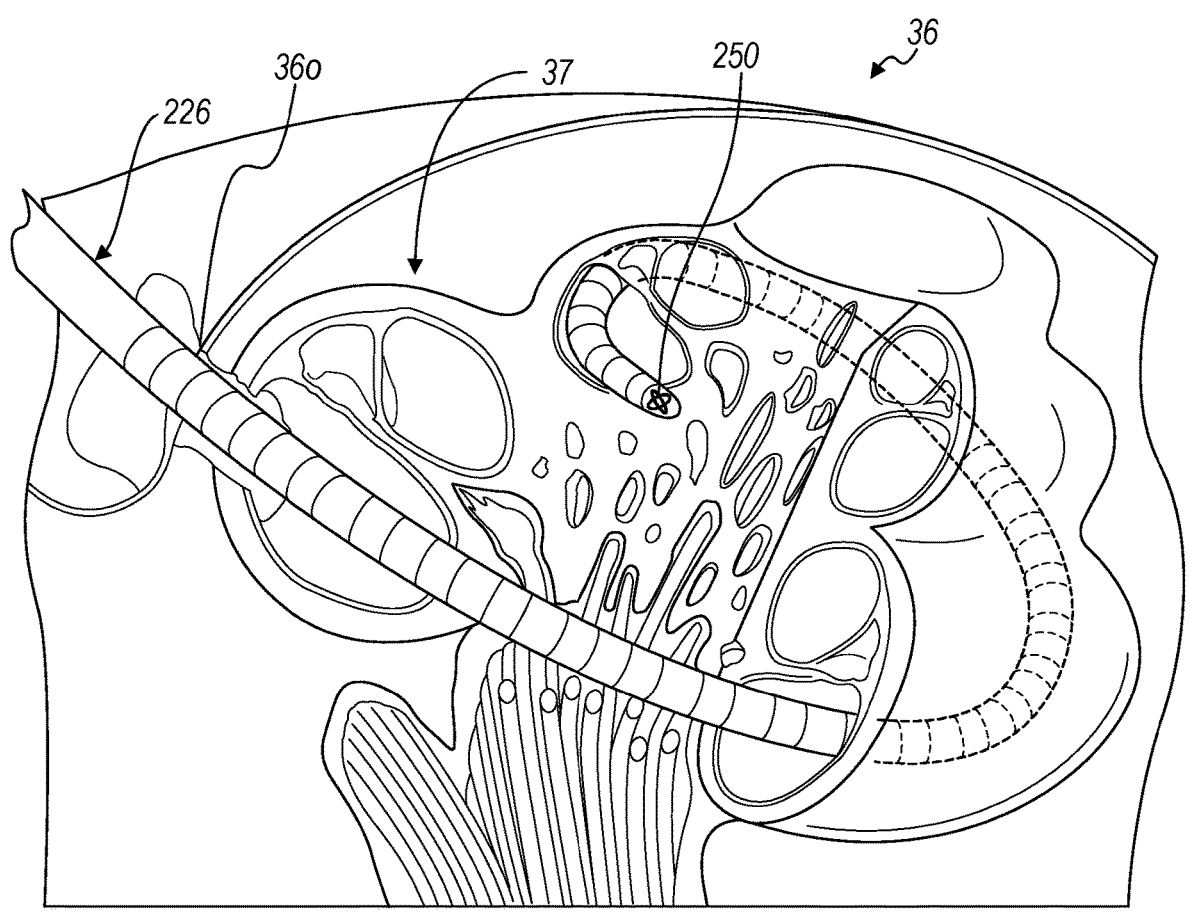
FIG. 4 is an environmental view of the instrument during implantation in the subject, according to various embodiments.

By providing the stimulation to the electrodes 232, external sound may be provided as stimulus to the subject 36 in an appropriate manner. During implantation, the cochlear implant 226 may be positioned through a small opening 36o, as illustrated in FIG. 2B and FIG. 4, into a cochlea 37 of the subject 36. The cochlear implant 226 may be flexible in an appropriate manner to be positioned within the cochlea 37 to achieve a shape of the internal space including a circular or internal winding, of the cochlea 37. Therefore, the cochlear implant 226 may include a selected flexibility to allow for implantation into the cochlea 37.

The opening 36o may include a small surgical opening that is only slightly larger than a diameter of the cochlear implant 226. For example, the cochlear implant 226 may have an external maximum diameter of about 0.1 millimeters (mm) to about 2 mm, including about 0.8 mm to about 0.1 mm, further including about 0.5 mm to about 0.2 mm. Further, the cochlear implant 226 portion that includes the electrodes 232 may taper from a maximum dimension to about 0.4 mm to about 0.8 mm. The opening 36o may therefore have an internal diameter that is about 0.1 to about 0.8 millimeter greater than the diameter of the cochlear implant 226. In various embodiments, the opening 36o may have an internal diameter that is about 1% to about 300%, including about 150%, greater than the external of the diameter of the cochlear implant 226. The size of the opening 36o, therefore, may not allow for direct visualization of the cochlear implant 226 as it is being positioned within the cochlea 37.

As discussed above, the navigation system 20 may allow for tracking of selected portions of the cochlear implant 226. For example, an EM tracking device 250 may be positioned at a distal end 254 of the cochlear implant 226. The EM tracking device 250 may be any appropriate EM tracking device, such as one including one or more coils of conductive material or wire. For example, the EM tracking device 250 may include three coils of wire, all on different axis, but having a common origin. EM tracking devices may be designed and configured to allow for a determination of six degree of freedom position (including location and orientation). Exemplary EM tracking devices include those disclosed in U.S. Pat. No. 8,644,907, incorporated herein by reference.

The EM tracking device 250 may be tracked by the EM tracking system 24. As discussed above, the EM tracking system 24 may include the localizer 76 to transmit or receive an EM field to allow for a determination of the EM tracking device 70*b*, which may include one or more of the tracking device 250. The tracking device 250 may be sized and configured to be positioned within an internal structure and/or not alter a generally understood external geometry of the cochlear implant 226 while allowing for tracking of the cochlear implant 226.

Furthermore, it is understood that a plurality of the devices 250 may be positioned along a length of the cochlear implant 226. For example, a plurality of the devices 250 may be positioned spaced apart about 0.1 millimeter (mm) to about 1 centimeter, including about 0.2 mm apart along the length of the cochlear implant 226. The tracking devices may be spaced apart along the body 230, such as spaced apart along a longitudinal axis of the body 230. For example, each of a plurality of these devices 250 may be positioned substantially adjacent to each of the electrodes 232 along the length of the body 230. Therefore, a defined or substantially precise position of the length of the body 230 of the cochlear implant 226 may be determined. Moreover, based upon registration of image data to the patient 36, the tracked and determined position of the cochlear implant 226 may be illustrated relative to the image 84 on a selected one or more display devices 38, 40.

Accordingly, in various embodiments, the EM tracking device 250, or a plurality of the devices 250, may be formed into the body 230 of the cochlear implant 226 to allow for a tracking of one or more points along a length of the cochlear implant 226. Tracking one or more of the devices 250 allows for a determination of a positon of the cochlear implant 226. The determined position of the cochlear implant 226 may then be illustrated relative to the image 84 illustrated on the selected display device 38, 40. Tracking the EM tracking device 250 with the EM tracking system 24 is generally understood in the art. As discussed above, the tracking device 250 may generate or sense an electromagnetic (EM) field while the localizer 76 operates in the reverse of the tracking device 250. A signal from the localizer 76 and/or the tracking device 250 is transmitted to the processor system 44, directly or through the CAC 72. Transmission of the signal may be wireless or wired, such as with a transmission line 76' from the localizer 76 and/or an appropriate transmission system (wireless or wired) from the EM tracking device 250. In various embodiments, the connectors 236 of the cochlear implant 226 may be connected to the EM tracking system 24, such as the CAC 72, to transmit a signal from the EM tracking device 250.

The signal from the tracking device 250 is used to determine the position (including three-dimensional location and one or more orientation in the space of the tracking device 250 and, therefore, the instrument 26). As discussed above, registration of the image data to the subject may be performed such that tracking of the cochlear implant 226 may allow for illustration of its position relative to the image 84.

With continuing reference to FIGS. 2B, 3, and 4, the position of the body 230 of the cochlear implant 226 may be determined by a plurality of the EM tracking devices 250, including a second EM tracking device 250' and a third EM tracking device 250". The plurality of tracking devices, as noted above, can be used to show or determine a specific position of a plurality of points along the length of the body 230. Therefore, a specific shape, such as a coiled shape, may be determined based on the plurality of spaced apart tracking devices. This will be used to determine the final location and when a selected location has been achieved of the implant 226.

Figure 5:
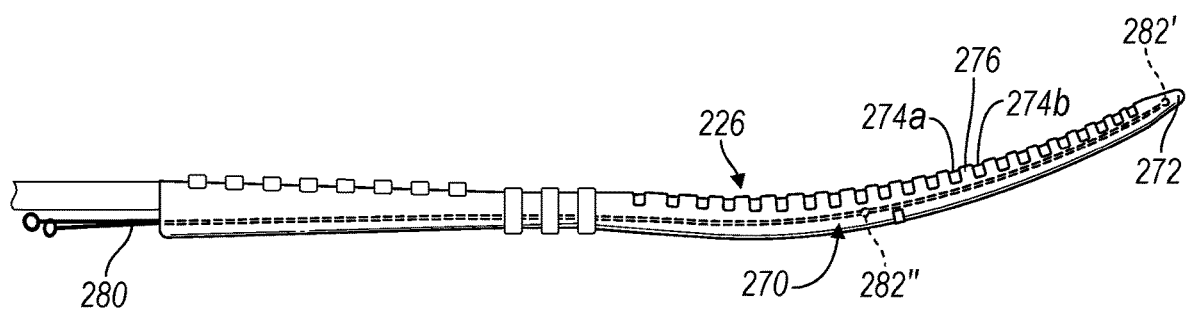
FIG. 5 is a detailed view of an instrument, according to various embodiments.

With additional reference to FIG. 5, in addition to, or alternatively to, providing the EM tracking device 70*b* as one or a plurality of the EM tracking devices 250 in the implanted member 226, the EM tracking device 70*b* may be provided as a temporary member or removable member. In various embodiments, the cochlear implant 226 may be positioned within a sleeve or flexible member, such as a silicone or other selected flexible material sleeve 270. The sleeve 270 may have a terminal end 272 that covers the end of the implant 226. The sleeve 270 may further include openings or gaps 274, such as a first gap 274*a* and a second gap 274*b*. The gaps may be separated by solid portions 276. The gaps 274 allow for access of the electrodes 232 to a portion of the patient 36, such as within the cochlea 37. The sleeve may be positioned over the implant 226 before positioning it into the cochlear, generally known in the matter. The sleeve 270 may form a portion of the implant, in such an instance.

A trackable stylet or guide wire 280 may be positioned within the sleeve 270 and may extend a distance into the sleeve 270, including to a terminal end 272. The guide wire 280 may include one or more EM tracking devices 70*b* such as a tracking device 282' and/or more tracking devices 282". The tracking devices 282 may include a plurality of tracking devices positioned along a length of the guide wire 280. For example, the tracking devices 282 may be spaced apart along a longitudinal axis of the guide wire 280. Therefore, the guide wire 280 may be positioned within the sleeve 270 during implantation of and positioning of the implantable member 226.

Once the final location of the implant 226 is achieved, the guide wire 280 may then be removed. When the guide wire 280 is removed, the sleeve 270 may remain in place with the cochlear implant 226. In various embodiments, the guide wire 280 may be removed at any time prior to final implant location being achieved to allow the implantable member 226 to achieve a shape or position within the cochlea 37. Because the guide wire 280 is removable, the tracking devices 282 need not be permanently included with the implantable member 226. The removal of the guide wire 280 also allows the cochlear implant 226 to be unchanged from a current configuration, but allows for tracking of at least a portion of the cochlear implant 226. Having the guide wire 280 with the implant while positioning it within the cochlea, however, may allow for tracking a position of the implantable member 226 during at least a portion of the implantation procedure.

The guide wire 280 may include one or more tracking devices 282. The tracking devices 282 may include those that are formed around an exterior of the guide wire 280, such as having a plurality of coils of a conductive material (e.g. wire) round around and along an axis, such as a long axis of the guide wire 280. The coils may be formed of conductive material, such as wire, wrapped around an exterior surface of the guide wire 280. Further, the wire may be wrapped at a selected angle to provide a differentiation of tracking axes relative to the longitudinal axis of the guide wire 280. Selected wrapping configurations and trackable portions include those disclosed in U.S. Pat. No. 8,644,907, incorporated herein by reference. The tracking members 282 may also or alternatively be individual coils of wire wound around a core having a size and shape (e.g. a diameter of about 0.1 mm to about 0.5 mm and length of about 0.5 mm to about 5.0 mm) to be positioned within the guide wire 280. The individual coils may be selectively placed within the guide wire 280 at selected positions, such as near a tip thereof and/or along its length. The tracking members 282, regardless of configuration, may be used to track the trackable member 226 to offer a determination of the position of a plurality of points of the trackable member 226, including a shape thereof. However, the guide wire 280 may be removed from the sleeve 270 prior to ending a procedure on the patient 36. By removing the guide wire, the implanted member 226 is configured to be positioned within the subject without permanently including the tracking devices 280.

The implantable body 226 may alternatively, or in addition to the EM tracking devices 70b, as discussed above, include the external sleeve 270. The sleeve 270, discussed above and illustrated in FIG. 5, may be permanently implanted with the implantable device 226. However, a removable or tracking sleeve 290 may be temporarily positioned over the implantable device 226 and/or over the sleeve 270. The tracking sleeve 290, as illustrated in FIG. 3, may include one or more of the EM tracking devices 70b, such as a first EM tracking device 294' and a second tracking device 294". The EM tracking devices 294', 294" may be formed with (e.g. molded into) the removable sleeve 290. The removable sleeve 290 may be formed of an elastic material and/or material that includes a substantially high coefficient of friction with the body 230. Therefore, the sleeve 290 may be maintained in a selected position relative to the implantable device 226 when positioning and moving the implantable device 226 into the patient 36. The removable sleeve 290, however, may be removed once the implantable device 226 is selectively positioned within the cochlea, such as with an open or frangible end.

As the implantable portion 226 is moved to and through the opening 36o toward the cochlea 37, the tracking device 294', 294" may be used to track the position of the sleeve 290. As the sleeve 290 moves with the implantable portion 226, the position of the implantable portion 226 can also be determined. The sleeve 290, formed of the material that remains substantially fixed relative to the implantable body 230, the tracking devices 294', 294" in the sleeve 290 are used to track the position of the implantable device 226. The sleeve 290 may be formed of selected material such as a biocompatible silicone. The material of the sleeve 290 may fixedly engage the implantable device 226 to be held relative to the implantable device 226 during implantation procedure. The sleeve 290, therefore, remains substantially fixed and does not move relative to the implantable member 226 more than an error tolerance of the tracking system 24 during implantation.

The tracking devices 294', 294" may be formed at discrete intervals along a length of the removable sleeve 290. Each of the tracking devices 294', 294" has a plurality of coils of conductive material for acting as EM tracking devices 70b. For example, the coils may be formed relative to one another on a surface of the sleeve 290. In various embodiments, the conductive material of the tracking devices 294' and 294" may be formed as windings around an exterior of the sleeve 290 along a longitudinal axis of the sleeve 290. The tracking devices 294', 294" may also be formed or provided as small coils and/or printed on, and/or formed as wire windings on the sleeve, as discussed above. Accordingly, the tracking devices 294', 294" may be formed substantially similar to the formation of the tracking devices of the guide wire 280. However, it is understood, that the tracking devices 294', 294" may be formed from individual and separate portions that are positioned or formed into a surface or wall of the sleeve 290.

After positioning the implantable member 226 in the cochlea 37, the sleeve 290 may be removed from the implantable device 226. A tab or leash 298 may be connected to the sleeve 290 and extend out through the opening 36o, as illustrated in FIGS. 2B and 3, to be grasped by the user or surgeon 34. After positioning the implantable device 226 within the patient 36, the leash 298 may be grasped and pulled to remove the sleeve 290 from the implantable device 226. The sleeve 290 may include a frangible or breakable portion, such as a perforated portion, such as perforation 302, at a distal end 290' of the sleeve 290. The perforation 302 may be opened or perforated by pulling on the leash 298 and the sleeve 290 at the perforation engaging the distal end 254 of the implantable device 226. When engaging the implantable member 226, the perforation may open to allow the sleeve 290 to be withdrawn over the implantable device 226 after positioning the implantable device 226 in the cochlea 37.

It is understood that other features may be provided to remove the sleeve 290 from the implantable device 226 to make certain that the sleeve 290 need not be maintained within the subject 36 after positioning the implantable device 226. For example, the terminal end may be open and the sleeve 290 may include features, e.g. a high co-efficient of friction material, to maintain the sleeve 290 fixed relative to the cochlear implant 226 during implantation. It is understood, however, the sleeve 290 may be maintained on the implantable device 226 during a lifetime of usage of the implantable device 226. The sleeve 290 may be formed of a biocompatible material similar to the sleeve 270. Moreover, it is understood that the sleeve 270 may include the tracking devices 294', 294" rather than providing the removable sleeve 290 as a separate and second sleeve.

According to various embodiments, wireless or wired transmission of a signal to the EM tracking system 24 may be made from the various EM tracking devices 70b. The EM tracking system 24 may receive a tracking signal to allow for determination of the location of the respective tracking devices and further to determine the tracked position of the instrument 26, including the implantable device 226. Various portions of the implantable devices 226 may be repurposed or re-tasked from the tracking during implantation to use of the implantable device 226 to stimulate the cochlea after implantation. For example, the implantable device 226, as discussed above, includes one or more wires 236 that are interconnectable to the plurality of electrodes 232 on the implantable device 226. The tracking signal from the respective tracking devices may be transmitted along the wire 236 prior to connecting the wire 236 from the cochlear implant 226 to the selected receiver and stimulator 234 that may be positioned with the patient 36, as is generally understood with a cochlear implant. Therefore, the wires 236 may be used both to transmit the signal from the tracking devices to the EM tracking systems 24 and later be disconnected from the EM tracking system 24 and connected to the receiver and stimulator 234 for operation of the implant member 226. As noted above, one or both of the internal R&S portion 234 and/or the external R&S 234a may transmit a signal from selected portions, such as the coils 250 and/or the electrodes 232 for tracking. It is understood that the coils 250 and/or electrodes 232 may communicate via signal through the internal R&S portion 234 and/or the external R&S 234a and, or alternatively, the connectors 233.

In addition to and/or alternatively to the EM tracking devices 70b, as discussed above, the EP tracking devices 70a may be provided with the implantable device 226. As discussed above one or more axis electrodes 60a-60c may inject a current into the subject 36. The current injected may be produce a voltage or impedance at one or more electrodes on the implantable device 226. For example, the implantable device 226, as discussed above, includes the one or more electrodes 232, where the electrodes 232 may be implant electrodes that are to stimulate the cochlea 37 once connected to the R&S 234. The electrodes 232 may transmit or send a signal along the conductive members or wires 233. As discussed above, the wires 233 may be connected to the EP tracking system 22 in a manner similar to connection to the EM tracking device 24. Accordingly, the wires 233 may be initially tasked or purposed as transmission wires for tracking the electrodes 232 and later may be connected to the stimulator and receiver for transmitting and/or receiving a signal from the receiver and/or stimulator associated with the patient 36. Similarly, the electrodes 232 may be initially tasked or purposed as EP tracking device 70a. After implantation, the electrodes and wires 233 may be re-tasked or repurposed as simulation electrodes for the cochlear implant system.

In the EP tracking system 22, the axis electrodes 60a-60c, or any appropriate number of axis electrodes 60, may inject a current into the subject 36. A voltage or impedance may be, due to the injected current, sensed at the one or more electrodes 232. With reference to FIGS. 2A, 2B, and additional reference to FIG. 5, the implant member 226 may be positioned within the cochlea 37. The cochlea 37 may include conductive or partially conductive fluids to allow a voltage to be sensed by one or more of the electrodes 232 based upon the injected current and from the axis electrodes 60. Although the axis electrodes 60a, 60b, and 60c are illustrated it is understood that more than three axis electrodes may be provided.

The axis electrodes each may inject a current, which may include an alternating current. The alternating current generates a voltage or electrical potential at each of the electrodes 232 on the implant device 226. Each of the axis electrodes 60a-60c may inject a current at a selected frequency, where each frequency may be different. Further, there may be a temporal or time differential between the injected current from each of the axis electrodes 60a-60c. In other words, the currents injected with the axis electrodes 60a-60c may be time or frequency multiplexed or differentiated. Therefore, the potential measured at each of the electrodes 232 may be triangulated relative to all of the individual axis electrodes 60a-60c. The relative position of each of the electrodes 232 to one another may be determined based upon the spaced apart position of each of the axis electrodes 60a-60c. This may allow the user 34 to operate the processor system 44 to determine a relative position of the implant device 226 during implantation. The user 34 may view the image 84 and the determined position of the implant device 226 may be displayed on the image 84.

The image 84 may be registered, as discussed above, to the implant device 226. The EP tracking system 24 may be registered to the image 84 using appropriate registration techniques, such as those discussed above. For example, an EP tracking device 70a may be positioned within the subject 36 at a known landmark to determine a registration to the image data by identifying the landmark on the image 84. Alternatively, or in addition thereto, one or more of the EM tracking devices 70b may be positioned at a same or known position relative to the EP tracking device 70a to allow for registration of the EP tracking device 70a and the EM tracking device 70b and, therefore, registration to the image 84. A co-registration with the EM tracking system 24 may be used to assist in registration, including the EP tracking system 22, to the image 84. For example, as discussed above, one or more of the EM tracking devices 70b may be placed with one or more of the axis electrodes 60a-60c. Thus, the location of the axis electrodes 60a-60c of the EP tracking system 22 may be determined with the EM tracking system 24 and, therefore, the location of the EP tracking device 70a that is tracked with the EP tracking system 22 may have its determined position translated to the EM tracking system 24.

Registration In this way, the image 84 may be registered with EM tracking system 24, which may include a substantially Euclidean geometry, which the EP tracking system may not include. As is understood by one skilled in the art, the EP tracking system including the current injected from the axis electrodes 60a-60c may not provide a purely Euclidean geometry of registration. It is understood, however, that exact registration may not be necessary if the user 34 selects to simply identify and/or understand the relative position of the electrodes 232 relative to one another during the implant procedure.

In addition, one or more of the EM tracking devices 70b may be associated with one or more of the axis electrodes 60a-60c. In various embodiments, as noted above, rather than a single solid member (e.g. a metal plate) used as the electrode 232, a coil of wire or other conductive material may be used to form the electrode 232. The coiled wire, if selected, may have a thickness that extends from a surface of the implant electrode 232 towards a central axis of the electrode 232. The outer most portion may act as the electrode pad of the electrode implant 232.

The coiled wire as the electrode may operate as the tracking device 70b with the EM tracking system 24. The position of the axis electrodes 60a-60c may, therefore, be tracked with the EM tracking system 24. The position of the electrodes 232 may be determined relative to the axis electrodes 60a-60c. This would allow the position of the electrodes 232, therefore, to be determined relative to a position with the EM tracking system 24. Thus, if the EM tracking system 24 is registered to the image, the position of the electrodes 232 may also be illustrated as an icon on the image 84.

By understanding a position of each of the electrodes 232 relative to one another, on the implantable device 226, the user 34 may understand the changing position of the implantable device 226. The user 34 may therefore understand and determine whether the implantable device 226 is achieving a selected shape, such as a pre-determined shape of the cochlea 37. Moreover, the user 34 can, prior to a procedure, understand and evaluate the image 84 of the subject 36 to predetermine a final desired orientation and position of the implant device 226. Therefore, by determining the relative position of the electrodes 232 of the implant device 226, the user 34 may determine whether a preselected shape, including location and/or orientation of the implant device 26, has been achieved.

Each of the electrodes 232 on the implantable portion 226 may be used to receive a voltage at the electrode based upon the injected current from the axis electrodes 60a-60c. This information may be used to resolve or determine a location and orientation of the implant device 226. A selected specific shape of the implantable device 226, as discussed above, may be selected to assist in assuring that the implantable device 226 is achieving the shape of the cochlea 37. To assist in determining the shape of the implantable device 226, with or without a determination of a location of the implantable device 226 relative to the subject 36, a relative capacitance between each of the electrodes 232 may be determined. As discussed herein, any first electrode and any second electrode of the electrodes 232 may form an arbitrary or selected pair of electrodes. A capacitance between each arbitrary pair of the electrodes 232 may be measured. A comparison of the capacitance between each arbitrary pair may be compared over time and at any instant in time to determine a relative distance between the arbitrary pair of electrodes. It is understood that a relative capacitance between any two of the electrodes of the implant electrode 232 may also be determined with a direct reading (such as with a volt meter) between the two electrodes (e.g. 232$i$ and 232$ii$). Thus, an injection of a current from the axis electrodes 60$a$-60$c$ is not necessary for a determination of a comparison of capacitance.

Figure 6:
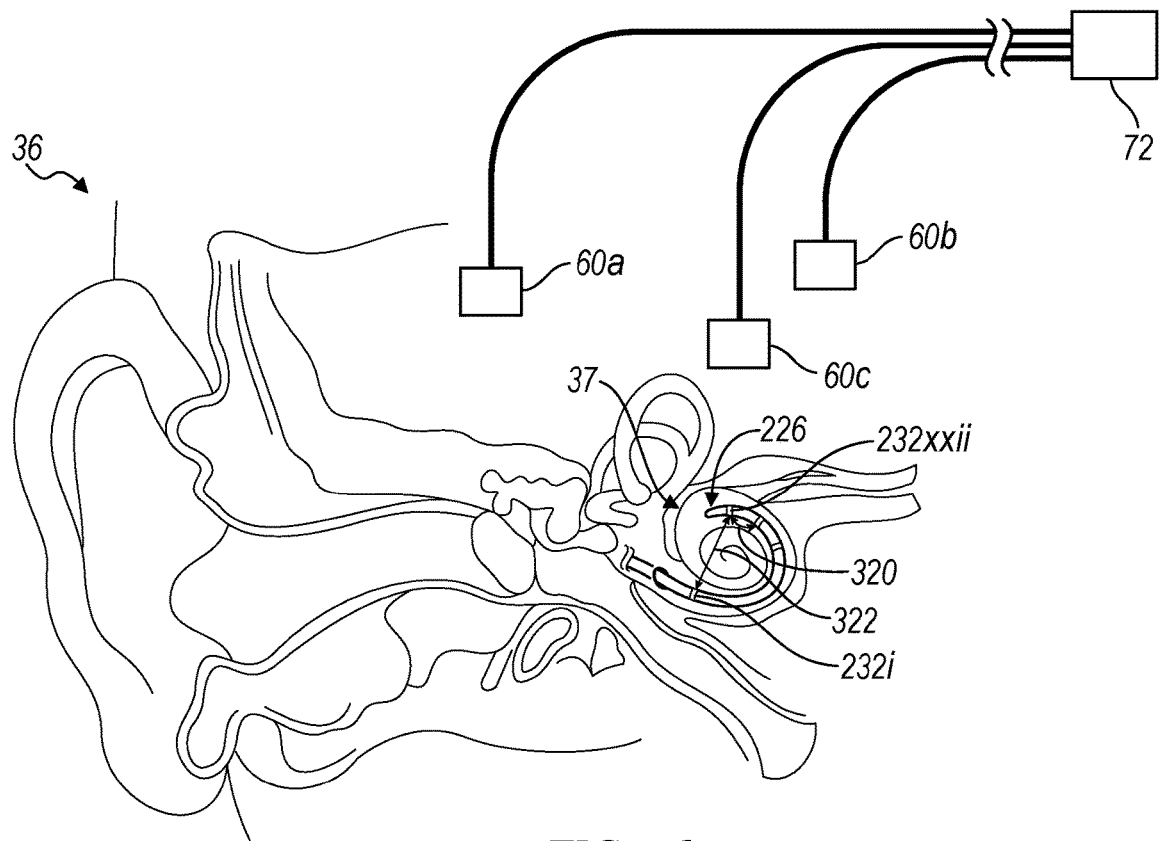
FIG. 6 is a detailed environmental view of an instrument, according to various embodiments.

Each of axis electrodes 60$a$-60$c$ positioned on an external surface of the patient 36 may be used to generate a potential relative to each of the electrodes 232 on the implantable device 226. For example, the axis electrodes 60$a$-60$c$ may be used to generate a relatively positive charge relative to the electrodes 232 on the implantable device 226. A determination of capacitance between any two of the electrodes 232 may be used to resolve and determine a shape of the implantable device 226 between the two electrodes 232. As the distance between two respective electrodes decreases, the capacitance between the same two electrodes increases. For example, with reference to FIG. 6, an initial distance between the electrode 232$xxii$ and 232$xxi$ may be achieved when the implantable device 226 is substantially straight and being initially inserted into the patient 36. As the implantable device 226 achieves the coil within the cochlea 37, the distance between the two electrodes 232$xxii$ and 232$xxi$ may change. As the two electrodes 232$xxii$ and 232$xxi$ get closer together, as they begin to coil within the cochlea 37, the capacitance between the two electrodes may increase. Therefore, a measurement of capacitance between any two selected electrodes, especially the electrode 232$xxii$ and 232$xxi$, can be measured and compared over time to determine that they are becoming closer to one another.

The capacitance may be determined between any two of the electrodes, therefore the capacitance between the electrode 232$xxii$ can also be determined relative to the electrode 232$xx$ and any other of the electrodes to the electrode 232$ii$. Again, a change in capacitance between the electrodes 232$xxii$ and all of the other electrodes may be measured and determined over time to assist in determining a shape of the implantable device 226. The processor system 44, including the memory 44$b$, may maintain a record of the changing capacitance over time and determine a shape of the implantable device 226, also over time. The determined shape may then be illustrated on the display device 38, 44 either alone or relative to the image 84.

In addition to determining a capacitance between two of the electrodes 232 of the implantable device 226, as discussed above with the injection of current from the access electrodes 60$a$-60$c$, a direct determination or sensing may also be made. As discussed above, the connectors 233 connect portions of the implantable device 226, such as each of the electrodes 232, to selected systems. The connectors 233 may connect to the selected tracking systems 22, 24 and/or the work station 44. It is understood that other appropriate measuring systems may also be included or associated with the various tracking systems 22, 24 and/or the work station 44. For example, a multi-meter may be used to directly connect the multi-meter to two or more of the electrodes 232. By connecting a selected meter to two or more of the electrodes, a direct calculation of a capacitance difference between two different electrodes may be determined. The measurement may be made between any or all pairs of the electrodes 232 of the implantable device 226, as discussed above. Accordingly, it is understood that the capacitance difference between two of the electrodes 232 need not be induced by the axis electrodes 60$a$-60$c$, but may be determined directly. Moreover, the EM localizer 76 may also be used to generate a field that may induce a voltage or capacitance difference between the electrodes 232 that may also be measured with a selected system, such as a selected multi-meter or other appropriate meter.

It is understood that each of the electrodes 232 on the implantable device 226 may be measured relative to any other of the electrodes on the implantable device 226. Therefore, the number of possible electrode pairs is also a function of the number of electrodes on the implantable device 226. Accordingly, the greater the number of electrodes the greater number of possible pair measurement may be made. The greater the number of electrode pairs, the greater resolution in determining a shape of the implantable device 226.

As discussed above, a capacitance between various electrodes may be determined, such as the electrodes 232 of the implantable device 226. The implantable device 226 including the selected number of electrodes 232, as noted above, or any appropriate number, may be used to determine a shape of the implantable device 226 in the patient 36, or any appropriate volume. The measurements may be based upon a shape determining algorithm and/or method, as discussed below, and as illustrated in the flowchart 360 in FIG. 7. To determine a shape of the implantable device 226 the capacitance between selected pairs of the electrodes, as noted above, may be determined and used to calculate the relative shape of the implantable device 226. It is understood that the relative shape of the implantable device 226 may be determined relative to any selected fixed or known point (e.g. tracked position), such as the location of one or more of the tracking devices 250 associated with the implantable device 226. Accordingly, a shape of the implantable device 226 may be determined according to method 360 illustrated in FIG. 7 and may be determined relative to a selected origin, such as one or more of the tracking devices 250.

In various embodiments, the method 360 begins at start block 364 and continues to determining a pairwise capacitance between selected electrodes 232 in block 368. In determining a pairwise capacitance between selected electrodes 232 it is understood that a capacitance may be determined between any two of the electrodes 232. For example, capacitance between the electrode 232$i$ and 232$ii$ may be determined as maybe a capacitance between electrode 232$i$ and 232$iii$ or 232$i$ and 234$iv$. Therefore, it is understood by one skilled in the art, pairwise capacitance between selected electrodes may include a determination of capacitance between all possible pairs of electrodes of the implantable device 226. Accordingly, the number of selected pairwise determinations may be based upon the number of electrodes included in the implantable device 226.

It is further understood, the greater number of pairwise capacitance determinations in block 368, the finer the determination of the shape of the implantable device 226 may be determined. For example, if a selected error or coarseness of the shape to be determined of the implantable device 226 is selected, a pairwise calculation between each of the electrodes may only be between every other electrode or appropriate number, such as one-half of the electrodes, one-third of the electrodes, or the like. If a finer shape determination is chosen, then a pairwise capacitance may be measured and determined between each electrode 232 and all of the other electrodes 232. Nevertheless, the pairwise capacitance determination may be made for electrodes along the length of the implantable device 226 for determining a shape along the length of the implantable device 226.

Once the pairwise capacitance measurements, from which the determinations may be made, between selected electrodes are completed in block 368, a calculated pairwise separation is made in block 372. The calculated pairwise separation may be between any of the pairs of electrodes for which a pairwise capacitance has been measured or determined in block 368. For example, a pairwise capacitance between all of the electrodes relative to each of the other electrodes may be made in block 368. The calculation of a pairwise separation may be made based upon the determined capacitance of the selected electrodes from block 368 in block 372. The determination of the pairwise separation may be based upon a known calculation or algorithm techniques such as direct computation, conformal conversions, auxiliary functions, and numerical approximations. Generally, the pairwise separation may be a distance or a radius (r) between two electrodes (i) and (j). Accordingly, a determination of the radius (r) between two electrodes may be illustrated or determined as $r_{ij}$. As discussed herein and illustrated in FIGS. 7A1 and 7A2, the radius r may define a circle relative to respective electrodes.

The determination of a shape of the implant device 226 may be determined based upon the calculated pairwise separations in light of the measured pairwise capacitances. The determination of the shape of the implantable device 226 may be made by initializing electrode relative positions (also referred to as determining an initial or initial guess position of the electrodes) in block 376. Initialization of the relative electrode positions may be made by selecting an origin electrode, such as the electrode 232$i$. It is understood that any appropriate electrode may be selected as the origin electrode and the electrode 232$i$ is merely exemplary. An initialization, however, need not be with a single one of the electrodes 232. Rather, it may be assumed that the implant electrode device 226 is a straight line and the shape determination algorithm and method, as discussed herein, may proceed from such an initialization.

Moreover, the shape of the implantable device 226 determined with a method 360, as illustrated in the flowchart in FIG. 7, may be used to calculate or determine a selected fine shape of the implantable device 226. However, a relative or absolute position of the implantable device 226 may be determined with alternative or separate tracking devices, such as the tracking device 250. Accordingly, the origin electrode may be near one of more of the tracking devices associated or connected with the implantable device 226.

With continued reference to FIG. 7 and in additional reference to FIG. 7A the initialization of the relative electrode positions in block 376 will be described in greater detail. FIG. 7A describes in greater detail the process of block 376. Accordingly, the method at 360 including block 376 includes the sub-steps or a sub-algorithm in block 376, as illustrated in FIG. 7A. As discussed above, a selection or placement of a single electrode at an origin position $P_i$ is performed in block 380. With continuing reference to FIG. 7A and additional reference to FIGS. 7A1 and 7A2, the position of electrodes are illustrated by dots and enumerated by $P_i$ or $P_{i+1}$ and $P_{i+N}$. It is understood that any appropriate number of the electrodes 232 may be determined and that the following discussion regarding the three electrodes is merely exemplary. Moreover, it is understood that the electrodes may have an initial or initiated position determined as $P_i$ and a relative position may then be determined, as discussed further herein.

With reference to FIG. 7A1, it is illustrate that the electrodes are in a straight line. It is understood, however, that the electrodes may be positioned in any three-dimensional relative positon, as illustrated in FIG. 7A2. Moreover, it is understood that a position of the electrodes may be constrained by various constraints, such as the anatomy of the subject. Accordingly, a returned or determined relative position of the electrodes may be based upon or limited to constraints determined relative to the anatomy of the subject 36. For example, as illustrated in FIG. 7A2, only one of the two orientations may be determined as possible and illustrated to the user 34, such as one that illustrates a branch to the right from the origin $P_i$. For example, as illustrated in FIG. 7A2, therefore, the electrode determined to be at the right (i.e. $P_{i+N(r)}$) may be determined to be the real or proper electrode position while the one to the left (i.e. $P_{i+N(l)}$) may be determined to not be the proper or correct possible electrode position. As discussed further herein, therefore, only one of a selected possible position of electrodes may be determined or returned or illustrated for a user.

The distance between the electrodes (as noted above defined by radius r) may be based upon a measured capacitance between different electrodes. Measured capacitance may be based upon an applied voltage on the implantable device 226 between the various electrodes and the implantation system. As discussed above, the implantable device 226 includes the communication line 233 to a controller, which may be included with the processor system 44. Accordingly, a capacitance between each of the electrodes may be measured and determined by the controller.

As illustrated in FIGS. 7A1 and 7A12, a determined distance or radius relative to each of the other electrodes. For example, the electrode $P_i$ includes a radius $r_{i(1)}$ relative to the second electrode $P_{i+1}$. The electrode $P_i$ also includes a radius $r_{i(2)}$ relative to the end electrode $P_{i+N}$. Similarly the electrodes $P_{i+1}$ and $P_{i+N}$ include radii relative to each of the other electrodes. It is understood, that only three electrodes is merely exemplary and for ease of the present discussion. As discussed further herein, the radii may be used to determine the relative positions of the electrodes.

Once the selection of a single electrode at the origin is performed in block 380, a first nearest neighbor electrode may also be "placed". In placing the first nearest neighbor, it is understood to be a determination of a spacing based on the measure capacitance between the selected electrode and the neighbor, here the first nearest neighbor. The placement of the first nearest neighbor (where the two electrodes are $\vec{p}^1(i-1)$ and $\vec{p}^1(i+1)$ is in a manner such that the following equations in Table 1 are satisfied.

TABLE 1

$r_{(i-1)i} \pm \varepsilon;$
$r_{i(i+1)} \pm \varepsilon;$ and
$r_{(i-1)(i+1)} \pm 2\varepsilon$ Error may be present in an amount due to measurement error, instrument error or an arbitrary amount to make the fit, error is represented by "$\varepsilon$". It is further understood that additional equations in a like manner may be provided or derived to calculate the position of all of the electrodes measure, as discussed below.

The implantable device 226 is positioned within the patient, or at least beginning to be positioned in the patient, and the determination of the position of the electrodes can assist in determining a shape of the implantable device 226 within the subject 36. Accordingly, the method 360 assists in determining the position or shape of the implantable device 226. The placement of the electrodes and the initiation of placement in block 376, therefore, allows for the determined shape of the implantable device 226. The placement or possible determination of the location of each of the electrodes may also include a slight amount of error indicated by $\varepsilon$. Accordingly, the calculated or checked position of the electrode may be the radius between the electrode including an amount of error (e.g. plus or minus ($\pm$)$\varepsilon$).

The determined position of the electrode may be between the origin or first electrode $P_i$ and any other electrodes, such as the electrode $P_{i+N}$. The determination may then further include the placement of all neighbors or the kth nearest neighbor with a less than or equal to k+1 nearest neighbor constraint in block 386. As discussed above, the constraints may include an amount of error to allow for a determination of the placement of the electrode relative to one another. Constrains may also include the positions determined of the tracking devices 70. For example, a shape of the implantable device 226 may be limited or constrained by a tracked and determined position of any selected tracking device. Additional constraints may include a selected or known rotational position of the electrodes in a shape relative to the patient or subject space. For example, as illustrated in FIG. 7A2 the electrodes may branch in a selected position, such as in a right or left direction. As the implantable device 226 is positioned in a selected portion of the patient 36, such as in the cochlea of the subject 36, the implantable device 226 may have a selected or known curve limitation. Accordingly, a constraint may include only returning or placing electrodes that curve in a selected direction, such as to the right as illustrated in FIG. 7A2. It is understood that the curve may be any appropriate curve or constrained shape and that a curve to the right is merely exemplary. Moreover, it is understood that the curve or branch position may be in three-dimensional space relative to any of the placed electrodes.

Finally, after placing all of the electrodes the electrode relative positions may be returned in block 390. Again, it is understood that the returned relative positions may be initialized positions in block 376 and that the detail sub-algorithm or steps illustrated in FIG. 7A are included in the initialization of the electrode relative position in block 376. Moreover, the placement of the electrodes is based upon the measured and determined capacitance between the electrodes in a pairwise manner. As noted above, it is understood that the position between the electrodes or distance between the electrodes may be based upon a measurement of a capacitance between all of the electrodes in a pairwise manner, or a selected number of the electrodes in a pairwise manner. The placement of electrodes may be based upon the process as discussed above and illustrated in FIG. 7A and FIGS. 7A1 and 7A2. The initialization of the relative electrode positions in block 376, however, may allow for a determination of a shape of the implantable device 226, as discussed further herein.

After initializing the electrode relative positions in block 376, as discussed above, adjustment of the electrode relative position to block 396 may occur. It is understood that adjusting the relative positions of block 396 is optional and not required for the method 360. Nevertheless, the adjustment of electrode relative positions in block 396 may also include various sub-steps or algorithm, as illustrated and discussed in detail with reference to FIG. 7B. The sub-steps illustrated and discussed in relation to FIG. 7B is understood to include or be included in block 396 of the method 360. In particular, the adjustment of the relative electrode position in block 396 may account for and redistribute error ($\varepsilon$) as discussed above. In particular, as noted above, the error may be incorporated into the placed or selected position for the electrodes 323. Accordingly, the error may not be initially or at first pass properly distributed amongst the electrodes. In other words, the error in a calculation, such as from a measurement, may be associated with one electrode more than another when determining the position of the electrode based upon the calculated radius relative to other pairwise electrodes. Redistributing the error may better identify the distance between pairwise electrodes and allow for a better determination of the shape of the implantable device 226.

Initially, in adjusting the electrode relative positions of block 396, a calculation of expected pairwise capacitances may be made in block 400. The calculation of expected pairwise capacitances may be based upon generally known calculations such as direct computation, conformal conversions, auxiliary functions, and numerical approximations. The calculated pairwise capacitances may be based upon the initialized placement of the electrodes in block 376. Accordingly, a calculation may be based upon the placement, including distance between, the electrodes 232. The calculation of the expected pairwise capacitance may be performed by a processor system, such as the processor system 44 as discussed above. An algorithm may calculate the expected pairwise capacitances based upon the calculation formula discussed above.

After calculating the expected pairwise capacitances in block 400, based upon the initialized tree from block 376, a difference between the expected capacitances and the measured capacitances may be made by receiving measured pairwise capacitances in block 402. Then, calculating a function ($F_o$) with the measured capacitances and difference to expected capacitances ($\Delta_{ij}$) in block 404. The function ($F_o$) may be any appropriate function, such as a least-squares function such as $\Sigma_{i,j,d \neq j}^{N} \{\Delta_{ij}(\vec{p}^1_i, \vec{p}^1_j)\}^2$. In particular, the function may be a sum of the differences between the measured and the expected capacitances between each pair of selected electrodes 232. Again, it is understood, that the pairs of electrodes may be a pair of each one electrode to each of the other electrode of any selected number of pairs of electrodes. Further, as discussed above, the measured capacitance and/or expected capacitance is based upon a distance between the electrodes. Given that the distance between a pair, a circle with the distance as a radius from the first electrode should intersect with a circle with the distance as a radius from a second electrode, as illustrated in FIGS. 7A1 and 7A2 of where the electrode actually lies in space relative to the other electrode in the pair. Accordingly, a difference between a measured and expected (as calculated as discussed above) capacitance may be due to a measurement error or a calculation error. Accordingly, the error E may be distributed amongst the selected or initialized position of the electrodes to provide a better fit and therefore minimize the function $F_o$.

Once the function is calculated or determined in block 404, the function may be optimized over electrode positions in block 406. As discussed above, the error may be included in a calculation or positioning of each of the electrode 232 in space as discussed and illustrated in block 376. Accordingly, distributing or applying more error to one electrode or another may optimize the fit or reduce the error between the expected and measured position of the various electrodes 232. The error may, therefore, be adjusted or moved between the different electrodes 232 of the pairwise calculation or determination in block 406.

The optimization of the function, including the distribution of error to minimize the function ($F_o$ below) may be done in a selected manner, such as selectively or randomly applying the error to different ones of the electrodes. In various embodiments, the error redistribution and/or determined shape may be adjusted by generally known random movements algorithms (e.g. a Monte Carlo method), local optimization methods (e.g. gradient descents), global optimization methods (e.g. parallel tempering), and pattern recognition methods (e.g. deep neural networks). It is understood, however, that other appropriate optimization algorithms may be used.

Accordingly, once the function $F_o$ is optimized in block 406, a determination of the optimized or determined relative electrode position may be made in block 410. The determined relative electrode positions may then be output in block 414. The output may be any appropriate output, such as a signal to the navigation system 22, 24, rendering a display, etc.

The relative electrode positions in block 376, including as adjusted, may be used to determine relative shape of the implantable device 226. As discussed above, the relative positions of the electrodes 232 that are fixed or positioned along the length of the implantable device 226 may be used to determine a relative shape of the implantable device 226. The adjusted electrode relative to position in block 396 may be used to determine or output a relative shape of the implantable device in block 420. The shape of the implantable device 226, as determined based upon the initialized electrode relative positions in block 376 and/or the option adjusted electrode relative positions in block 396, is a relative shape of the implanted device 226. Generally, as discussed above, the implantable device 226 may be positioned or initially positioned relative to the subject 36. Accordingly, the shape of the implantable device 226 determined in block 420 may be used to determine the shape of the implantable device 226 within the patient 36.

The determined relative shape of the implantable device 226 relative to the patient 36 may then be combined with position information of the implantable device 226 to determine a position of the implantable device 226 relative to the patient 36. A combination of the shape determined in block 420 and the determined position may be combined in block 424. The determined position of the implantable device 226 may be based upon various tracking devices such as the tracking device 70 (e.g. tracking device 250). As discussed above, the tracking devices 70 associated with the implantable device 226 may be registered to the patient 36 and/or the image 84.

For example, the tracking device 250 associated with the implantable device 226 may be used to determine location of at least one point or portion of the implantable device 226. Therefore, the position of at least one point on the implantable device 226 is known relative to the patient 36. The determined shape from block 420 may be known relative to the tracking device 250. Accordingly, the shape of the implantable device 226 relative to the tracked location of the tracking device 250 is known or combined in block 424. Again, the determined shape in block 420 and the combination of the shape and determined position in block 424 may be formed by executing instructions with the processor system 44a using the tracking information from the tracking device 250 and the determined shape from block 420.

Once combined in block 424, a determined position and shape combined in block 424 may be output in block 428. The output shape and position may be displayed as an icon (e.g. 26i) on the display device 40 including the image 84. It is understood that the icon may be displayed on other display devices, but may generally be illustrated as an icon relative to image data of the subject 36. For example, as discussed above, the tracked location of the tracking device 250 may be registered to the patient 36. The patient (defining patient space or subject space) may be registered to the image 84 (defining image space). Accordingly, as the tracked location of the tracking device 250 is known relative to the image 40 and the shape is determined relative to the tracking device 250 the determined shape of the implantable device 226 may be displayed as an icon on the image 40. The user 34 may view the determined shape and position of the implantable device 226 on the image 40 for assisting and determining whether the implantable device 226 is properly located in a selected or final location.

As discussed above, it is understood that the method 360, including the various sub-algorithms or portions as discussed above, may be provided as algorithms and instructions executed by the processing system 44 including the processor 44a. The algorithm, as discussed above, may be executed by the processor 44a based upon instructions stored on the memory 44b. The processor system 44, therefore, may allow for a fast and efficient manner of determining the shape of the implantable device 226 within the patient 36 while not directly viewable by the user 34 and/or imageable by an imaging system. Accordingly, the method 360 allows for the processor system 44 to efficiently and quickly determine a shape of the implantable device 226 and a position of the shape of the implantable device 226 for use during a selected procedure or operation.

The shape of the implantable device 226 may also be otherwise determined and/or estimated. For example, an estimate of the shape of the implantable device 226 may be made with a single EM tracker, such as the EM tracker 250 at the tip of the implantable device 226. The previously tracked positions of the EM tracking device 250 may be used to determine or estimate a shape of the implantable device 226. The trace of previous and/or current positions of the EM tracking device 250 may be displayed with or without a current determined position of the EM tracking device 250 with the display device. In addition to or alternatively to the single tracking device, multiple tracking devices may have positions determined simultaneously and/or over a past period of time. The past "traced" positions may be determined as a shape or a best fit to the past determined positions may be made. Again, the determined shape may be displayed if selected. For example, the shape may be displayed as an icon superimposed on the image 84.

With continuing reference to FIGS. 1-6 and additional reference to FIG. 8, the implantable device 226 may include a plurality of the electrodes 232. Each of the electrodes may be formed as small coils, as discussed above, which may be operated in a selected field or emit a selected field to assist in tracking the location of each of the electrodes 232. As generally understood by one skilled in the art, the coils may sense an electromagnetic field and generate a signal based upon the sensed field. Alternatively the coils may emit a field that is sensed by a receiver. Regardless, the location of each of the electrodes 232 may be determined.

In various embodiments, even if the electrodes 232 are solid or single piece members, one or more of the electrodes 232 may be connected together. It is understood that each of the electrodes is connected to the communication line 233. The communication line 233, as discussed above, may allow for communication with the R&S 234 and/or other systems, such as the EP or EM tracking system 22, 24. As discussed above, signals from the electrodes 232 may be transmitted to the respective tracking systems 22, 24 for selected position determination.

Further a connection 450 may be formed between one or more of the electrodes 232. For example, and merely for ease of the following discussion, a first connection 450a may be between the second electrode 232ii and the third electrode 232iii to form a first electrode coil 460. Further, a connection 450b may be formed between the fourth electrode 232iv and the fifth electrode 232v to form a second electrode coil 462. A third or alternative connection may interconnect more than two of the electrodes 232, such as the connection 452 that interconnects the sixth electrode 232 vi and the ninth electrode 232ix to form a third electrode coil 466. The connection 452 may, therefore, not connect or be in contact with the electrodes between the sixth electrode 232vi and the ninth electrode 232ix. Further, the connections, such as the connection 450 and 452 may electrically connect the selected electrodes. In this manner, the first electrode coil 460 may be smaller than the third electrode coil 466. The larger electrode coil 466 may generate a stronger signal or higher signal-to-noise ratio than the smaller electrode coil 460.

The electrode to electrode connections 450, 452 may be formed in any appropriate manner. For example, a permanent or breakable connection may be formed between each of the electrodes such as with a wire or other conductive manner. Further, the connections 450, 452, according to various embodiments, may be formed on the sleeve 290 such as with a trace or other appropriate mechanism to temporarily connect selected ones of the electrodes 232, but are removable once the sleeve 290 is removed from the implantable device 226. As discussed above, the sleeve 290 may be positioned on the implantable device 226 for positioning the implantable device 226 within the patient 36. The sleeve 290 may include traces that form the connections 450, 452 between selected ones of the electrodes 232. The connections 450, 452 may be substantially passive, and not be used to generate or transmit a signal or power or form a potential relative to other portions. The connections 450, 452, as discussed further herein, may simply be used to connect to the selected ones of the electrodes 232. The connections of the electrode 232 to the communication line 233 may be used to transmit or receive a signal relative to the selected electrodes 232.

With continuing reference to FIG. 8, an implantable device 226a may be substantially similar to the implantable device 226 illustrated in FIG. 3. The implantable device 226a, however, may not include the EM tracking device 250. Nevertheless, various portions of the implantable device 226 may be operated in combination with the EM tracking system 24 to provide for a determination of the position and/or orientation of the implantable device 226a. The implantable device 226a, including the communication line 233, may communicate with the EM tracking system 24 to communicate a signal to the processor system 44 to assist in determining a location of at least a portion of the implantable device 226, according to various embodiments, as discussed herein.

According to various embodiments, the connections 450a and 450b may connect to respective electrodes, such as adjacent electrodes. It is understood, however, that the connection 450a and 450b may not connect to adjacent electrodes or may not connect only two electrodes. As discussed above the connection 452 may connect more than one electrode. Nevertheless, a signal from one or more electrode coils may be transmitted. Although the connected electrodes may be referred to herein as coils, it is understood that the coils may be formed due to the respective connections, such as the connection 450a between the electrodes 232ii and 232iii, and a single from the coil portion may be transmitted on the communication line 233 to the EM tracking system 24. The connection 450a in combination with the two electrodes 232ii, 232iii forms the coil 460. Similarly the coil 462 is formed due to the connection 450b and a single coil 466 may be formed due to the connection 452 between the electrodes 232vi to 232ix. It is understood that the coil 466 may be an effectively larger coil relative to the coils 460, 462. It is further understood, other coils may be formed by connections between the other electrodes in the implantable device 226 and that the illustrated ones are merely for use in the current discussion.

The coil 460 and 462 may be operated as two separate coils with the EM navigation system 24. The signal from the coils 460, 462 may be transmitted on the communication line 233 to the EM navigation system 24, as discussed above. The coils may operate in the EM navigation system 24 similar to other generally known coils, as discussed above, in EM navigation systems. Accordingly, one skilled in the art will understand that the coils 460, 462 may be operated to sense a field (e.g. have a current induced in the coil due to an externally generated field) and/or emit a field to be sensed by a receiver. A signal transmitted through the communication line 233 may be used by the EM navigation system 24 to transmit to the processor system 44 and/or any appropriate processor system to determine a location of the coils 460, 462. The individual location of either of the coils 460, 462 may be determined based upon the received signal.

In an alternative and/or complementary operation, a differential signal between the two coils 460, 462 may be used to determine the position and orientation of the two coils 460, 462. In other words, a signal regarding the difference in the sensed fields between two nearly adjacent or adjacent coils may be transmitted. This differential signal may reduce or eliminate the effect of noise or interference on the transmitted signal.

Accordingly, it is understood, that the coils 460, 462 may be operated in more than one operational manner to assist in determining a position of one or more of the coils 460, 462. The position of the implantable device 226, however, may be determined based upon a signal from the coils 460, 462 either individually and/or as a differential signal between the two coils 460, 462. Accordingly, the electrodes 232 may be operated as at least a pair to form a coil that may be used with the EM navigation system 24 to assist in determining a location of the coils 460, 462. It is further understood that all of the electrodes 232 may be combined as selected pairs to form coils along the length of the implantable device 226.

Furthermore the coil 466 may be formed based upon a connection 452 of more than two of the electrodes 232. It is further understood that any selected number of the electrodes 232 may be connected to form a coil of a selected size. Therefore any appropriate or a selected number, such as ten or twelve of the electrodes 232 may be combined to form a coil. Regardless of the number of the electrodes connected, however, the connected or large coil 466 may also transmit a signal on the communication line 233 to the EM navigation system 24. The signal to the EM navigation system may be used to determine a location of the coil 466 to the determined location of the implantable device 226. Again, the coil 466 may operate in a manner substantially similar to a coil as discussed above in the EM navigation system.

Therefore, one skilled in the art will understand that one or more coils may be formed in the implantable device 226 to be used by the EM navigation system 24 to determine a position (e.g. a location and orientation) of the implantable device 226 based upon a determined location and orientation of one or more of the coils 460, 462, 466.

In addition to the position information determined by the EM navigation system 24 due to the coils 460, 462, 466, a shape of the implantable device 226 may also be determined as discussed above. Accordingly, the position of the implantable device 226 may be used to determine a location relative to the subject 36, in a manner similar to using the tracking devices 250, as discussed above. However, the tracking devices 250 may be eliminated from the implantable device 226a and one or more of the electrodes 232 may be combined to form a selected coil, such as the coil 460, and a shape of the implantable device 226a may be determined in a manner somewhat similar to that as discussed above. Therefore a tracking device, such as the tracking device 250 may not be incorporated as a separate element relative to the implantable device 226a to determine a location of the implantable device 226a.

In addition, with reference to FIG. 3 and/or FIG. 8, each of the electrodes 232 may communicate with the EM tracking system 24. The EM tracking system including a localizer array may generate a field that is sensed by or generates a potential difference across two electrodes, such as the first electrode 232i and the second electrode 232ii. Although, the two electrodes 232i, 232ii are not connected with a conductive member associated or formed by the implantable device 226, the electrodes may be in electrical communication due to the environment in which they are placed. For example, the electrodes 232 are positioned or may be positioned within the subject 36. The subject 36 may include an amount of conductivity where a potential difference may be determined and transmitted to the EM tracking system 24. The induced voltage may be based upon the field emitted by the localizer the EM navigation system 24 and may be used by the EM navigation system 24 to determine the position of the tracking device or the potential differential between the two electrodes 232i and 232ii. Again, one skilled in the art will understand that the electrical connection between the electrodes 232i and 232ii may form or allow for the determination of a potential differential to allow for tracking or determining a location of the electrodes similar to the tracking devices 250 in the EM tracking system, as discussed above.

Accordingly, it is understood that tracking devices 250 may not need to be incorporated into the implantable device 226, such as the implantable device 226a. Nevertheless the included electrode 232 may be used with the EM tracking system 24 to determine a position (e.g. a location and orientation) of at least a portion of the implantable device 226. This position may be used alone and/or in combination with a determined shape of the implantable device 226, as also discussed above. Moreover, the position of the implantable device 226 may be illustrated as an icon superimposed on the image 84 of the subject 36 once the position and/or shape are determined. Therefore, the user 34 may be able to view the determined position and shape of the implantable device 226 during a procedure.

Accordingly, the implantable device 226 may be positioned within the cochlea 37 to be tracked with selected tracking systems, such as the EP tracking system 22 or the EM tracking system 24. As discussed above, selected EM tracking devices 70b may be associated with the implantable device 226, either incorporated into the implantable device 226 or provided in the removable member 290 relative to the implantable device 226. The EM tracking device 70b may be tracked with the EM tracking system 24 to assist in determining the position of the implantable device 226 and a shape of the implantable device 226, such as within cochlea 37. In such systems, the transmission line 233 may be repurposed or re-tasked from an initial transmission of tracking device signals, during implantation of the implantable device 226, to transmitting simulation signals when connected with the receiver and stimulator as a part of the cochlear stimulation system.

In addition to, or alternatively to, the EM tracking device 70b, the electrodes 232 of the implantable device 226 may be used in the EP tracking system 24 to resolve various features of the implantable device 226. For example, the shape of the implantable device 226 may be determined based upon relative capacitance between various electrodes 232 of the implantable device 226, as discussed above. Thus, a shape of the implantable device 226 may be determined when positioning the implantable device 226 in the cochlea 37. Further, the electrodes 232 of the implantable device 226 may be used with axis electrodes, such as the axis electrodes 60a-60c, to determine a position of the implantable device 226 within the patient 36. The determined position of the implantable device 226 using the EP tracking system 24 may be registered to the image 84 or may be illustrated or determined relative to the axis electrodes 60a-60c. It is understood by one skilled in the art that the EP tracking system 22 is not required to register to the image 84, but may be tracked relative to the axis electrodes 60a-60c positioned on the patient 36. In any case, the shape and/or position of the implantable device 226 may be determined by measuring the voltage and/or capacitance at the individual electrode 232 along the length of the implantable device 226.

Further, the translation or distance between the respective EM tracking devices and the EP tracking devices can be determined using selected external or additional image modalities. For example, fluoroscopy can be used to determine a distance between two tracking devices if both of the tracking devices are radio opaque. Although it can be selected to eliminate or substantially reduce the use of ionizing radiation during a procedure, such as may be used in fluoroscopy, fluoroscopy can be minimally used to determine certain information.

Additional imaging systems can also be used to obtain information of the patient 36 or information regarding the mapping or trackable devices. Imaging systems can include ultrasound (US), computed tomography (CT), magnetic resonance imaging (MRI), and other appropriate imaging techniques can be used. For example, an US system can be used to image or view the position of the selected tracking device within the patient 36. An US transducer can be used to view the tracked device and determine its position in the patient 36. Accordingly, selected imaging systems can be used to image the location of the instrument within the patient 36. As discussed above, this can also be used to determine a distance between two tracked devices within the patient 36, such as for translation or registration purposes between the two tracking systems 22, 24.

The R&S 234 may also include various wired or wireless communication systems for communicating with one or both of the tracking systems 22, 24. The implantable device 226, which may be placed in a cochlea of the subject 36, may be connected to the R&S 234 during implantation of the implant 226. A signal from any of the selected tracking devices 70a (e.g. electrode 232), 70b (e.g. tracking device 250), as discussed above, may be communicated to the R&S 234. The signal may relate to various sensed fields, capacitances, etc., as discussed above. The signal may be communicated wirelessly to the respective tracking systems 22, 24. Thus, a direct connection of the tracking devices 70a, 70b from the cochlear implant 226 to the respective tracking systems 22, 24 may not be necessary as a communication may be made first to the R&S 234 then to the respective tracking systems 22, 24. The wireless transmission may be any appropriate transmission such as one using known Bluetooth® transmission protocols and hardware, a wireless network (e.g. local area network) hardware and/or protocol or scheme such as IEEE 802.11 wireless LAN systems, or other appropriate communication systems and protocols.

As illustrated above, image data may be acquired of the subject. The image data may be used to generate the image 84 for display on the display device 40, or any appropriate display device. In various embodiments the user 34 may view the image 84 and make a determination of a selected or predetermined shape of the implantable device 226 once positioned in the patient 36. The user 34 may enter or save the predetermined shape in the memory 44b by entering the selected shape or predetermined shape with an input, such as the keyboard 48. It is understood that the selection or predetermination of a shape of the implantable device 226 may be made at any appropriate time and need not be made in an operating theater, as illustrated in FIG. 1.

Nevertheless, a predetermined shape may be transferred to the memory 44b for accessing with the processor 44a. Accordingly, the predetermined shape of the implant 226 may be illustrated relative to the image 84, such as with an icon superimposed on the image 84. During the procedure, such as during positioning the implantable device 226 in the patient 36, the determined shape and/or position, as discussed above, of the implantable device 226 may be illustrated on the display 40. The user 34 may then compare the determined or tracked position and/or shape of the implantable device 226 relative to the predetermined position and/or shape. Moreover, the work station 44 may execute instructions stored on the memory device 44b to make a comparison, such as a fit comparison, of the determined shape and/or position to the predetermined shape and/or position. A percent or coefficient of matching of the present and tracked shape of the implantable device 226 relative to a predetermined shape may be displayed.

Moreover, the user 34 may make a determination (e.g. in real time) based upon the determined position and/or shape of the implantable device 226 displayed on the display device 40 whether it is a selected shape. Accordingly, the user 34 may view the display 40, or other appropriate selected display, during the procedure relative to the image 84. The user 34 may then view whether the shape of the image 84 is a selected shape.

Accordingly, the tracking of the location of the implantable device 226 and the method of determining the shape, as discussed above, may be used to efficiently perform a procedure to reduce procedure times and/or confirm or select appropriate or optimal locations for the implantable device 226.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method to track an implantable cochlear stimulator electrode assembly, comprising:
    evaluating a capacitance between a first electrode portion and a second electrode portion along a length of the implantable cochlear stimulator electrode assembly;
    determining a relative position of the first electrode portion and the second electrode portion based the evaluated capacitance;
    initializing a possible position of the first electrode portion and the second electrode portion;
    optimizing the determined positions of the first electrode portion and the second electrode portion based on the initial possible positions of the first electrode portion and the second electrode portion; and
    displaying on a display device a shape of the implantable cochlear stimulator electrode assembly at least between the first electrode portion and the second electrode portion based on determined optimized positions of the first electrode portion and the second electrode portion.

2. The method of claim 1, further comprising:
    injecting a current into a subject to measure the capacitance.

3. The method of claim 1, wherein evaluating the capacitance between a first electrode portion and a second electrode portion along a length of the implantable cochlear stimulator electrode assembly includes connecting a meter directly to the first electrode portion and the second electrode portion and measuring at least one of a capacitance at each of the first electrode portion and the second electrode portion or measuring a difference in capacitance between the first electrode portion and the second electrode portion.

4. The method of claim 1, wherein the first electrode portion and the second electrode portion includes a plurality of implant electrode portions, the method further comprising:
    evaluating a capacitance between each electrode portion of the plurality of implant electrode portions spaced apart along a length of the implantable cochlear stimulator electrode assembly and all other electrode portions of the plurality of implant electrode portions, wherein the first electrode portion and the second electrode portion are two electrode portions of the plurality of electrode portions;
    determining a relative position between each electrode portion of the plurality of electrode portions and each other electrode portion of the plurality of electrode portions based on the determined capacitance; and
    determining a shape of the implantable cochlear stimulator electrode assembly based on the capacitance between each of the plurality of implant electrode portions.

5. The method of claim 1, further comprising:
    operating at least one of the first electrode portion and the second electrode portion to transmit a stimulation to a cochlea of the subject after implantation of the implantable cochlear stimulator electrode assembly.

6. The method of claim 2, further comprising:
    operating a localizer positioned near the subject in which the implantable cochlear stimulator electrode assembly is to be positioned to measure the capacitance based on the injected current.

7. The method of claim 6, further comprising:
    measuring the capacitance with the localizer.

8. The method of claim 1, further comprising:
    providing the implantable cochlear stimulator electrode assembly with the first electrode portion and the second electrode portion along a length of the implantable cochlear stimulator electrode assembly.

9. A method to track an implantable cochlear stimulator electrode assembly, comprising:
providing the implantable cochlear stimulator electrode assembly with a first electrode portion and a second electrode portion along a length of the implantable cochlear stimulator electrode assembly;
providing the first electrode portion and the second electrode portion to have a relative position therebetween be determined based on an evaluated capacitance therebetween;
providing and operating a processor system having stored instructions thereon, wherein the instructions include;
initializing a possible position of the first electrode portion and the second electrode portion;
optimizing the determined positions of the first electrode portion and the second electrode portion based on the initial possible positions of the first electrode portion and the second electrode portion; and
displaying on a display device a shape of the implantable cochlear stimulator electrode assembly at least between the first electrode portion and the second electrode portion based on determined optimized positions of the first electrode portion and the second electrode portion.

10. The method of claim 9, further comprising:
providing a display device to display a shape of the implantable cochlear stimulator electrode assembly at least between the first electrode portion and the second electrode portion based on the determined optimized positions.

11. The method of claim 9, further comprising:
providing a localizer to inject a current into a subject to allow for a measurement of the capacitance.

12. The method of claim 11, further comprising:
providing the localizer to measure the capacitance.

13. The method of claim 12, wherein the first electrode portion and the second electrode portion includes a plurality of implant electrode portions, the method further comprising:
providing the localizer to evaluate a capacitance between each electrode portion of the plurality of implant electrode portions spaced apart along a length of the implantable cochlear stimulator electrode assembly and all other electrode portions of the plurality of implant electrode portions, wherein the first electrode portion and the second electrode portion are two electrode portions of the plurality of electrode portions;
wherein a relative position between each electrode portion of the plurality of electrode portions and each other electrode portion of the plurality of electrode portions is operable to be determined based on the determined capacitance; and
wherein a shape of the implantable cochlear stimulator electrode assembly is operable to be determined based on the capacitance between each of the plurality of implant electrode portions.

14. The method of claim 13, further comprising:
providing at least one of the first electrode portion and the second electrode portion to transmit a stimulation to a cochlea of a subject after implantation of the implantable cochlear stimulator electrode assembly.

15. An implantable cochlear stimulator electrode assembly operable to be tracked, comprising:
a first electrode portion at a first position along a length of the implantable cochlear stimulator electrode assembly;
a second electrode portion at a second position along the length of the implantable cochlear stimulator electrode assembly;
a first connection to the first electrode portion;
a second connection to the second electrode portion;
wherein a capacitance between the first electrode portion and the second electrode portion is operable to be determined; and
a shape determining system having a processor configured to:
determine the capacitance between the first electrode portion and the second electrode portion;
determine a relative position of the first electrode portion and the second electrode portion based the determined capacitance;
initializing a possible position of the first electrode portion and the second electrode portion;
optimizing the determined positions of the first electrode portion and the second electrode portion based on the initial possible positions of the first electrode portion and the second electrode portion;
wherein a shape of the implantable cochlear stimulator electrode assembly at least between the first electrode portion and the second electrode portion is operable to be determined based on determined optimized position of the first electrode portion and the second electrode portion.

16. The system of claim 15, further comprising:
a display device configured to display a shape of the implantable cochlear stimulator electrode assembly at least between the first electrode portion and the second electrode portion based on the determined optimized positions.

17. The system of claim 16, further comprising:
an injection system configured to inject a current into a subject to measure the capacitance.

18. The system of claim 15, wherein the shape determining system includes:
a meter connected directly to the first electrode portion and the second electrode portion to measure at least one of a capacitance at each of the first electrode portion and the second electrode portion or measuring a difference in capacitance between the first electrode portion and the second electrode portion.

19. The system of claim 15, wherein at least one of the first electrode portion or the second electrode portion is configured to transmit a stimulation to a cochlea of a subject after implantation of the implantable cochlear stimulator electrode assembly.

* * * * *

UNITED STATES PATENT AND TRADEMARK OFFICE
CERTIFICATE OF CORRECTION

PATENT NO. : 11,484,714 B2
APPLICATION NO. : 17/020141
DATED : November 1, 2022
INVENTOR(S) : Ishan Ann Tsay et al.

It is certified that error appears in the above-identified patent and that said Letters Patent is hereby corrected as shown below:

In the Specification

Column 9, Detailed Description, Line 30, Delete "positon" and insert --position-- therefor Column 13, Detailed Description, Line 53, Delete "24" and insert --22-- therefor Column 15, Detailed Description, Line 52, Delete "access" and insert --axis-- therefor Column 18, Detailed Description, Line 4, Delete "positon," and insert --position,-- therefor Column 18, Detailed Description, Line 48, Delete "$\vec{p}^1(i-1)$ and $\vec{p}^1(i+1)$," and insert --$\vec{p'}(i-1)$ and $\vec{p'}(i+1)$-- therefor Column 18, Detailed Description, Line 48, Before "is", insert --)--

Column 20, Detailed Description, Line 37, Delete "$\Sigma_{i,j,d\neq j}^{N} \{\Delta_{ij}(\vec{p}^1{}_i, \vec{p}^1{}_j)\}^2$," and insert --$\sum_{i,j,i\neq j}^{N} \{\Delta_{ij}(\vec{p'}_i, \vec{p'}_j)\}^2$.-- therefor Column 20, Detailed Description, Line 53, Delete "E" and insert --ε-- therefor Column 26, Detailed Description, Line 12, Delete "24" and insert --22-- therefor Column 26, Detailed Description, Line 23, Delete "24" and insert --22-- therefor Signed and Sealed this
Fifth Day of September, 2023

Katherine Kelly Vidal
*Director of the United States Patent and Trademark Office*